(12) United States Patent
Fukuyo et al.

(10) Patent No.: US 9,488,827 B2
(45) Date of Patent: Nov. 8, 2016

(54) SPECTRAL DEVICE

(75) Inventors: Fumitsugu Fukuyo, Hamamatsu (JP);
Michiharu Yonezawa, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 931 days.

(21) Appl. No.: 13/574,103

(22) PCT Filed: Jan. 6, 2011

(86) PCT No.: PCT/JP2011/050122
§ 371 (c)(1),
(2), (4) Date: Aug. 22, 2012

(87) PCT Pub. No.: WO2011/089931
PCT Pub. Date: Jul. 28, 2011

(65) Prior Publication Data
US 2012/0314295 A1    Dec. 13, 2012

(30) Foreign Application Priority Data

Jan. 21, 2010 (JP) ................................ P2010-011012

(51) Int. Cl.
*G02B 26/00* (2006.01)
*G01J 3/02* (2006.01)
(Continued)

(52) U.S. Cl.
CPC .......... *G02B 26/007* (2013.01); *G01J 3/0235* (2013.01); *G01J 3/12* (2013.01); *G01J 3/32* (2013.01); *G01N 21/64* (2013.01); *G01J 2003/1226* (2013.01); *G01J 2003/1243* (2013.01);
(Continued)

(58) Field of Classification Search
CPC .......... G02B 5/20; G02B 5/201; G02B 5/28; G02B 5/281–5/283; G02B 5/285–5/289; G02B 26/007–26/008; G01J 3/0202; G01J 3/0227; G01J 3/06; G01J 2003/068; G01J 2003/1213; G01J 2003/1217; G01J 2003/1221; G01J 2003/1226; G01J 2003/1231; G01J 2003/1243; G01J 2003/1247; G01N 21/64; G01N 2021/6471; G01N 2021/6419; G01N 2021/6463
See application file for complete search history.

(56) References Cited

U.S. PATENT DOCUMENTS 4,084,909 A      4/1978 Mathisen
4,176,916 A  * 12/1979 Carpenter ............... 359/589
(Continued)

FOREIGN PATENT DOCUMENTS

CN      1514930      7/2004
CN      1839332      9/2006
(Continued)

*Primary Examiner* — Kimberly N Kakalec
(74) *Attorney, Agent, or Firm* — Drinker Biddle & Reath LLP

(57) ABSTRACT

The object is to easily expand a variable range of selective wavelengths without enlarging a device. A spectral device 1 of the present invention includes four band pass filters 11a to 11d through which a light L2 from a light source 3 is selectively transmitted within a wavelength range according to an incident angle of the light L2, and a tabular rotary table 10 in which the band pass filters 11a to 11d are installed upright on a principal surface 10a, and which is made rotatable around a rotational center $C_1$ along the principal surface 10a, and the four band pass filters 11a to 11d are respectively disposed so that optical incidence planes 12 or optical emission planes 13 are inclined with respect to lines connecting the rotational center $C_1$ on the principal surface 10a of the rotary table 10 and center points 15a and 15d of the band pass filters 11a to 11d.

6 Claims, 21 Drawing Sheets

(51) Int. Cl.
  *G01J 3/32* (2006.01)
  *G01J 3/12* (2006.01)
  *G01N 21/64* (2006.01)
  *G02B 5/28* (2006.01)

(52) U.S. Cl.
  CPC ............... *G01N2021/6419* (2013.01); *G01N 2021/6463* (2013.01); *G01N 2021/6471* (2013.01); *G02B 5/28* (2013.01)

(56) References Cited

U.S. PATENT DOCUMENTS

| | | | |
|---|---|---|---|
| 6,936,805 B2 | 8/2005 | Ahn | |
| 2003/0063280 A1 | 4/2003 | Ando et al. | |
| 2003/0138199 A1 | 7/2003 | Ahn | |
| 2011/0267678 A1* | 11/2011 | Erdogan | G02B 26/007 359/290 |
| 2011/0280013 A1* | 11/2011 | Tafas et al. | 362/232 |

FOREIGN PATENT DOCUMENTS

| | | |
|---|---|---|
| JP | S53-012345 | 2/1978 |
| JP | 55-149023 | 11/1980 |
| JP | 62-22034 | 1/1987 |
| JP | H4-113235 | 4/1992 |
| JP | 4-326026 | 11/1992 |
| JP | 5-45993 | 2/1993 |
| JP | 6-59200 | 3/1994 |
| JP | H6-281813 | 10/1994 |
| JP | 9-68660 | 3/1997 |
| JP | 2003-106899 | 4/2003 |
| JP | 2003-241113 | 8/2003 |
| JP | 2003-283045 | 10/2003 |
| JP | 2003-315690 | 11/2003 |
| JP | 2004-184674 | 7/2004 |
| TW | I240794 | 10/2005 |
| TW | I279529 | 4/2007 |

* cited by examiner

SPECTRAL DEVICE

TECHNICAL FIELD

The present invention relates to a spectral device for selecting light in a predetermined wavelength range, and in particular, relates to a spectral device having dielectric thin film interference filters built-in.

BACKGROUND ART

A spectral device utilizing an interference filter in which dielectric thin films having different refractive indices are alternately laminated and its intermediate cavity layer is formed of a dielectric thin film having an intermediate refractive index has been conventionally known (refer to the following Patent Document 1). This spectral device has an interference filter provided so as to be freely turnable and changes an incident angle to the interference filter when parallel light rays are made incident to the interference filter, so as to continuously change its transmissive wavelength.

As one having a similar configuration, a wavelength-variable filter in which its wavelength variability according to an incident angle is achieved by rotating a rotary table provided with dielectric multilayer filters and controlling an incident angle of parallel light to the dielectric multilayer filters, has been known (refer to the following Patent Document 2). This wavelength-variable filter achieves an output of transmitted light having a broader wavelength range by adopting a configuration in which four filters are disposed so as to be rotationally symmetric on the rotary table.

CITATION LIST

Patent Literature

Patent Document 1: Japanese Patent Application Laid-Open No. S62-22034
Patent Document 2: Japanese Patent Application Laid-Open No. 2004-184674

SUMMARY OF INVENTION

Technical Problem

However, in the wavelength-variable filter including the plurality of filters disclosed in Patent Document 2 described above, it is unlikely to expand a variable range of transmissive wavelengths due to the interference among the plurality of filters when rotating the rotary table. This is caused due to the fact that, when an attempt is made to take a large incident angle of a filter, the incident light easily interferes with other filters, thereby limiting a range of incident angles to each filter.

Therefore, the present invention has been implemented under such a problem, and has an object to provide a spectral device which is capable of easily expanding a variable range of selective wavelengths without enlarging the device.

Solution to Problem

In order to attain the above object, a spectral device according to the present invention includes n (where n is an integer of 3 or more) dielectric thin film interference filters through which light from a light source is selectively transmitted within a wavelength range according to an incident angle of the light, and a tabular rotary supporting member in which the dielectric thin film interference filters are installed upright on a principal surface, and which is made rotatable around a predetermined point along the principal surface, and the n dielectric thin film interference filters are respectively disposed so that end planes on optical incidence sides or optical emission sides are inclined with respect to lines connecting the predetermined point on the principal surface of the rotary supporting member and center points of the dielectric thin film interference filters on the principal surface. In addition, the term "dielectric thin film interference filter" means a filter whose central wavelength denoting the performance of the filter is shifted according to an incident angle to the filter.

According to the above spectral device, light is made incident along the principal surface of the rotary supporting member from the light source, and the light is selectively transmitted through the dielectric thin film interference filters within a wavelength range according to an incident angle to the dielectric thin film interference filters, to be output. At this time, by rotating the rotary supporting member centering on the predetermined point of the principal surface, it is possible to alternately switch between each of the n dielectric thin film interference filters through which the light is transmitted, and it is possible to change the incident angle of the light to each of the n dielectric thin film interference filters, as a result, it is possible to continuously change the transmissive wavelength. In particular, provided that the dielectric thin film interference filters are disposed so that end planes thereof are inclined with respect to the lines connecting the predetermined point on the principal surface and the center points of the dielectric thin film interference filters, the interference among the plurality of dielectric thin film interference filters is reduced within a broad range of rotation angle, as a result, it is possible to easily expand a variable range of selective wavelengths without enlarging the rotary supporting member.

Advantageous Effects of Invention

According to the present invention, it is possible to easily expand a variable range of selective wavelengths without enlarging the device.

BRIEF DESCRIPTION OF DRAWINGS

FIG. 1A shows a case where the incident angle is 0 degrees,
FIG. 1B shows a case where the incident angle is 25 degrees,
and FIG. 1C shows a case where the incident angle is 50 degrees.

FIG. 13A shows a case where the incident angle is 20 degrees, FIG. 13B shows a case where the incident angle is 35 degrees, and FIG. 13C shows a case where the incident angle is 50 degrees.

DESCRIPTION OF EMBODIMENTS

Figure 1:
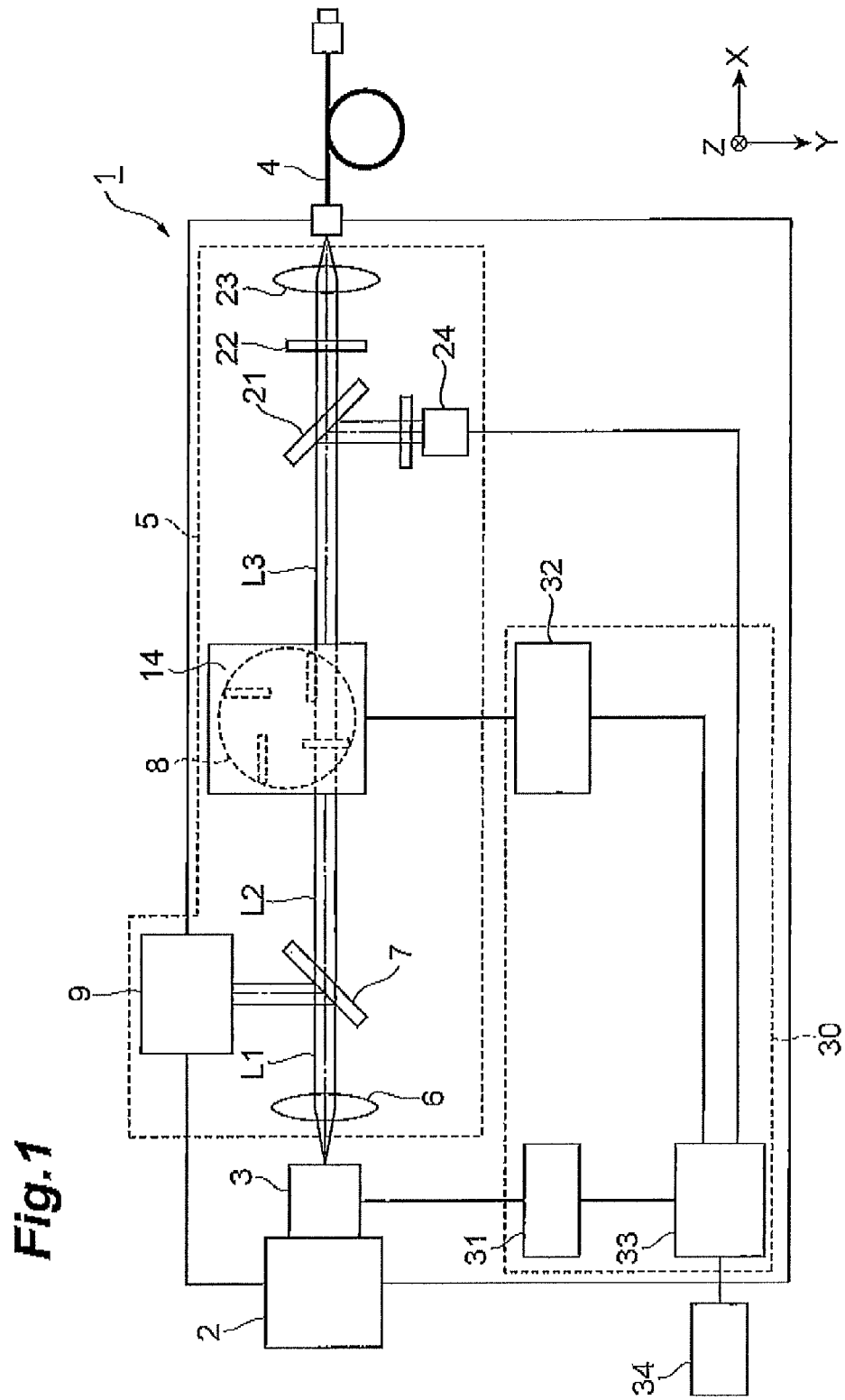
FIG. 1 is a plan view showing a schematic configuration of a light source device according to a first embodiment of the present invention.

Preferred embodiments of a spectral device according to the present invention will be described hereinafter in detail with reference to the drawings. In the description of the drawings, the same or corresponding parts are represented by the same reference numerals, and overlapping description is omitted. Further, the respective drawings are prepared for explanation, and are drawn so as to particularly put emphasis on objective regions for the explanation. Therefore, the dimension ratios of the respective members in the drawings are not necessarily matched to the actual dimension ratios.

[First Embodiment]

FIG. 1 is a plan view showing a schematic configuration of a light source device according to a first embodiment of the present invention. A light source device 1 shown in the drawing is a device used as a light source having a specific emission wavelength range (for example, near-infrared wavelength range) in various types of inspection devices such as semiconductor inspection devices. This light source device 1 is an aspect of a spectral device selecting a specific wavelength range in light from a light source, and is composed of a light source 3 attached onto a heat sink 2 serving as a radiation mechanism, a light conversion optical system 5 to which light irradiated from the light source 3 is made incident, and which converts the light to output the light to the outside via an optical fiber 4, and a control system 30 that controls the light source 3 and the light conversion optical system 5. Here, in FIG. 1, the X axis is set in a direction along the optical axis of the light source 3 on the sheet surface, the Y axis is set in a direction vertical to the X axis on the sheet surface, and the Z axis is set in a direction vertical to the X axis and the Y axis.

The light source 3 is a light source device such as a halogen lamp or a white LED including a predetermined wavelength range broadly from visible light components to infrared light components as an emission wavelength range, and the light source 3 emits a diffusion light in an unpolarized state toward the light conversion optical system 5 located in the +X axis direction.

First, the configuration of the light conversion optical system 5 will be described. In this light conversion optical system 5, a collimator lens 6, a wavelength-selective element 7, and a filter rotating body 8 are provided in order along the +X axis direction from the vicinity of the light source 3.

The diffusion light from the light source 3 is converted into a parallel light L1 by the collimator lens 6, to be incident to the wavelength-selective element 7. The wavelength-selective element 7 is an element for selecting light having a predetermined wavelength range (for example, 350 nm to 750 nm) in the parallel light L1 having the emission wavelength range of the light source 3 as a wavelength range, and is, for example, a dichroic mirror through which light having the predetermined wavelength range is transmitted, and by which light having ranges other than the wavelength range is reflected. This wavelength-selective element 7 is disposed so that its reflection face is inclined with respect to the X axis. When the parallel light L1 is made incident from the collimator lens 6, the wavelength-selective element 7 causes a light L2 having a predetermined wavelength range to be transmitted therethrough in the +X axis toward the filter rotating body 8, and reflects the light having wavelength components other than the predetermined wavelength range in the −Y axis direction as unnecessary light, to cause the light to disappear with a beam damper 9. In addition, the wavelength range selected by the wavelength-selective element 7 is set so as to include at least a wavelength-variable range (for example, from 400 nm to 700 nm. Hereinafter called "assumed wavelength range") of light finally output from the light source device 1.

Here, the structure of the filter rotating body 8 will be described in detail with reference to FIG. 2.

The filter rotating body 8 is composed of a rotary table (rotary supporting member) 10 which is a disk-shaped member which is rotatably supported by a rotating mechanism 14 having a rotary shaft along the Z axis, and four band pass filters 11a, 11b, 11c, and 11d which are installed upright so as to be rotationally symmetric along its peripheral edge on a principal surface 10a of the rotary table 10.

Figure 3:
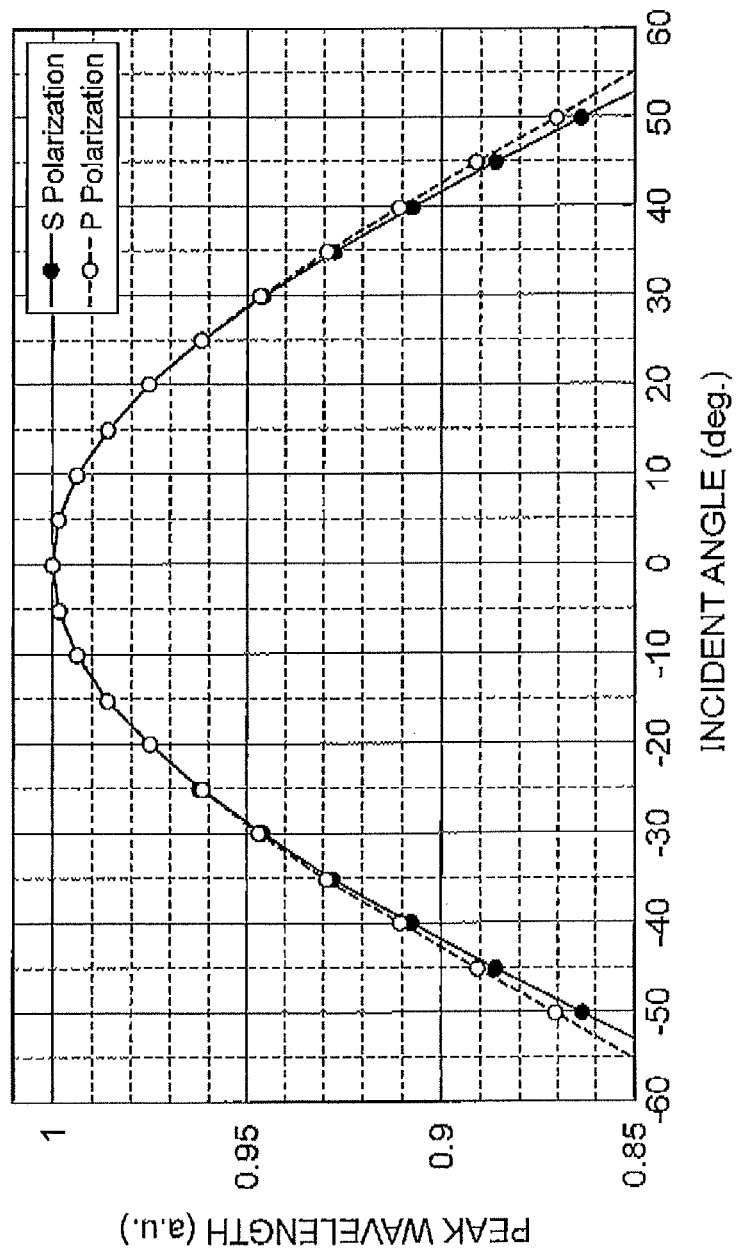
FIG. 3 is a graph showing the incident angle dependences of a peak wavelength in a transmissive wavelength range of band pass filters included in the filter rotating body of FIG. 2.

These band pass filters 11a, 11b, 11c, and 11d are so-called dielectric thin film interference type filters having tabular shapes, which contain a well-known laminated structure of dielectric thin films between an optical incidence plane 12 and an optical emission plane 13. With such a configuration, the band pass filters 11a, 11b, 11c, and 11d are capable of causing light to be selectively transmitted therethrough in a wavelength range corresponding to an incident angle of light to the optical incidence plane 12. Then, the materials and film thicknesses of the respective dielectric thin films are set so that the characteristics of the transmissive wavelength ranges are different according to an incident angle among the four band pass filters 11a to 11d. For example, in the case where the incident angle of light to the optical incidence plane 12 is 0 degrees, the band pass filter 11a has the characteristics of the transmissive wavelength range whose central wavelength is approximately 700 nm and whose half bandwidth is several nm. As the incident angle is increased, the transmissive wavelength range is shifted to the short wavelength side. In the case where the incident angle is 50 degrees, the band pass filter 11a has the characteristics of the transmissive wavelength range whose central wavelength is approximately 600 nm. Further, the band pass filters 11b, 11c, and 11d respectively have their characteristics of the transmissive wavelength range whose central wavelengths are approximately 610 nm, approximately 530 mm, and approximately 460 nm in the case where the incident angle is 0 degrees, which are different from that of the band pass filter 11a. FIG. 3 shows the incident angle dependences of a peak wavelength in the transmissive wavelength ranges of the band pass filters 11a to 11d with respect to S-polarized and P-polarized incident lights. In this way, as an absolute value of incident angle is increased with reference to the peak wavelength at an incident angle of 0 degrees, the peak wavelength is decreased, and its rate of change is increased as an absolute value of incident angle is increased.

Returning to FIG. 2, the band pass filters 11a to 11d having the above-described configuration are fixed so that the optical incidence plane 12 and the optical emission plane 13 are substantially vertical to the principal surface 10a of the rotary table 10. In detail, the band pass filters 11a to 11d are set so that lines connecting center points 15a to 15d on the principal surface 10a of the band pass filters 11a to 11d and a rotational center $C_1$ of the principal surface 10a are respectively inclined with respect to the optical incidence planes 12 and the optical emission planes 13 of the band pass filters 11a to 11d, and the inclination angles become equal to one another. Moreover, the band pass filters 11a to 11d are set so that four lines of intersections 16a to 16d formed between the respective optical emission planes 13 and the principal surface 10a contact one virtual inscribed circle 17, and the center points 15a to 15d of the band pass filters 11a to 11d are located lateral to the inscribed circle 17. In addition, the band pass filters 11a to 11d are disposed so that the four lines connecting the center points 15a to 15d and the rotational center $C_1$ form angles equal to one another, that is, 90 degrees therebetween. That is, the four band pass filters 11a to 11d are disposed so as to be four-fold rotationally symmetric centering on the rotational center $C_1$ on the principal surface 10a.

Further, rotary shaft members 18a to 18d such as shaft members or screw members may be attached in the vicinity of the center points 15a to 15d to the band pass filters 11a to 11d in order to fine-adjust the inclination angles of the optical incidence planes 12 and the optical emission planes 13 to the lines connecting the center points 15a to 15d and the rotational center $C_1$.

The filter rotating body 8 having the above-described structure is disposed so that the principal surface 10a is made parallel to the X-Y plane, and the light L2 is made incident to a space between the rotational center $C_1$ on the principal surface 10a and the peripheral edge portion of the principal surface 10a. Thereby, it is possible to rotate any one of the band pass filters 11a to 11d, to locate it on the optical path of the light L2, so as to make the light L2 be selectively incident thereto, and it is possible to change an incident angle to the band pass filters 11a to 11d within a predetermined angle range. The variable range of incident angles to each of the band pass filters in this case is determined by a beam width of the light L2, the number of band pass filters, and the shape and layout of the band pass filters.

Returning to FIG. 1, in the light conversion optical system 5, a beam sampler 21, a shutter 22, and a condenser lens 23 are provided in order in the +X axis direction along the optical axis of a light L3 transmitted therethrough by the filter rotating body 8. The light L3 is partially reflected by the beam sampler 21, and is guided by a power monitor 24, and its optical intensity is monitored. On the other hand, the light L3 is guided to the optical fiber 4 via the beam sampler 21, the shutter 22, and the condenser lens 23, to be irradiated to the outside.

Next, to describe the configuration of the control system 30, the control system 30 is composed of a light-source power supply 31 for supplying electricity to the light source 3, a drive circuit 32 for rotary-driving the rotating mechanism 14, and a control circuit 33 which is connected to the light-source power supply 31, the drive circuit 32, and the power monitor 24.

A computer terminal 34 is connected to the control circuit 33, which makes it possible to output an optical intensity value monitored by the power monitor 24 to the computer terminal 34, and it is possible to adjust an amount of light from the light source 3 by adjusting an output of the light-source power supply 31 according to a control signal from the computer terminal 34.

Further, the control circuit 33 also has a function of controlling a rotating angle of the rotating mechanism 14 according to a control signal from the computer terminal 34. At this time, the control circuit 33 controls a rotating angle of the rotating mechanism 14 and changes it so that the incident angle to the band pass filters 11a to 11d becomes a predetermined angle. This rotating angle is determined so as to correspond to a central wavelength of an emission wavelength range finally output from the light source device 1.

Figure 4:
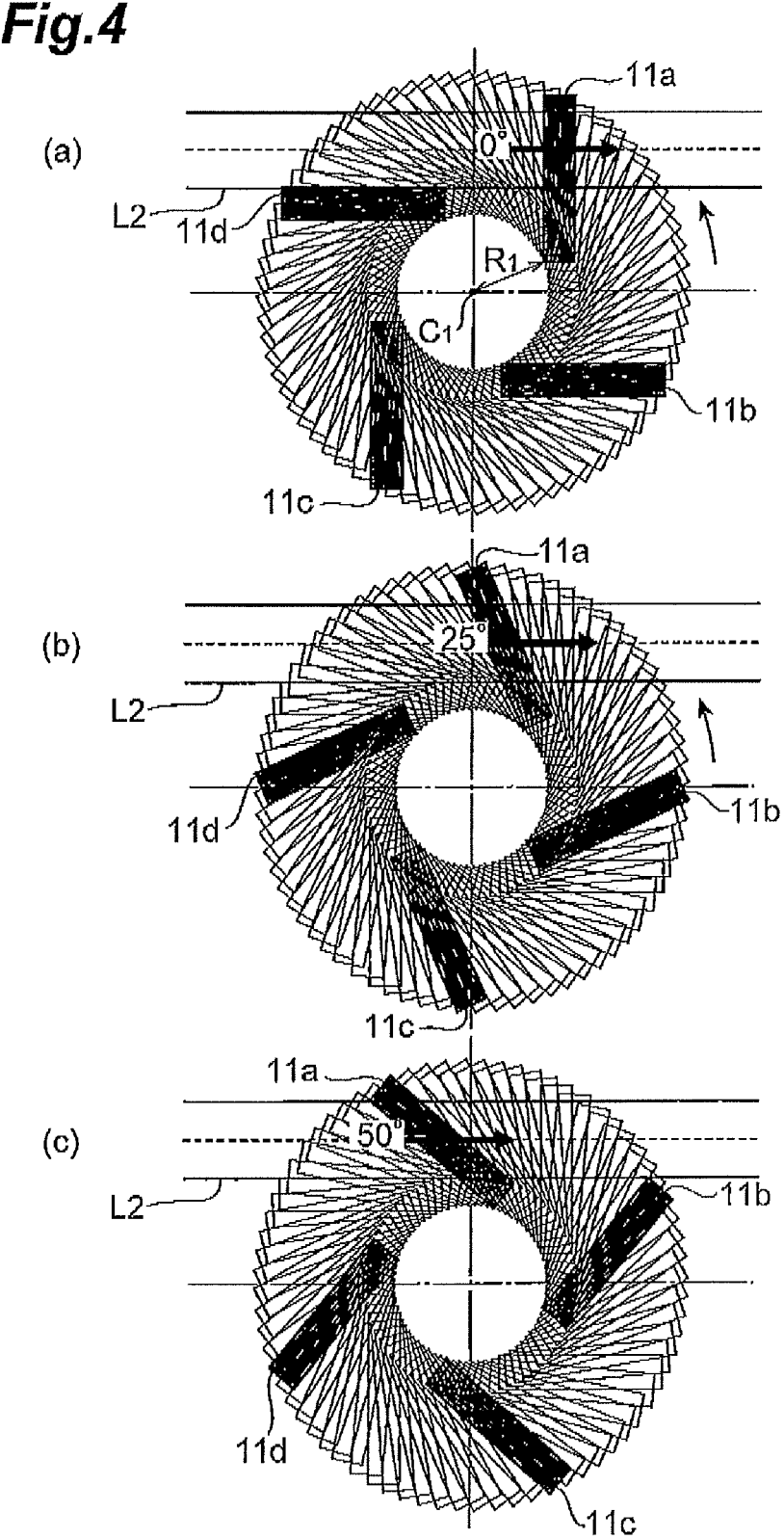
FIG. 4 are diagrams showing states of incidence of light to the band pass filter of FIG. 1.

With reference to FIG. 4, a variable range of incident angles to the band pass filter 11a is exemplified. The drawings show the states of incidence of the light L2 to the band pass filter 11a in the case where the beam diameter of the light L2 is 5 mm, the width and the thickness along the principal surface 10a of the band pass filter 11a are 11 mm and 2 mm, and the shortest distance $R_1$ from the rotational center $C_1$ to the band pass filter 11a is 16.6 mm. First, FIG. 4A shows the case where the incident angle to the band pass filter 11a is 0 degrees, and because the other band pass filters are not located on the optical path of the light L2, there is no interference among the band pass filters 11a to 11d in any case. Further, FIG. 4B shows the state in which the band pass filters 11a to 11d are rotated in a counterclockwise direction, to set the incident angle to the band pass filter 11a to 25 degrees, and FIG. 4C shows the state in which the band pass filters 11a to 11d are further rotated in a counterclockwise direction, to set the incident angle to the band pass filter 11a to 50 degrees, and there is no interference among the band pass filters 11a to 11a in both cases. When the band pass filters 11a to 11d are further rotated from the state of FIG. 4C, the band pass filter 11b gets on the optical path of the light L2. Therefore, the respective transmissive characteristics interfere with each other between the two band pass filters 11a and 11b, which makes it impossible to obtain a stable emission wavelength. Accordingly, the variable range of incident angles to each of the band pass filters 11a to 11d in this case is from 0 degrees to 50 degrees.

Figure 5:
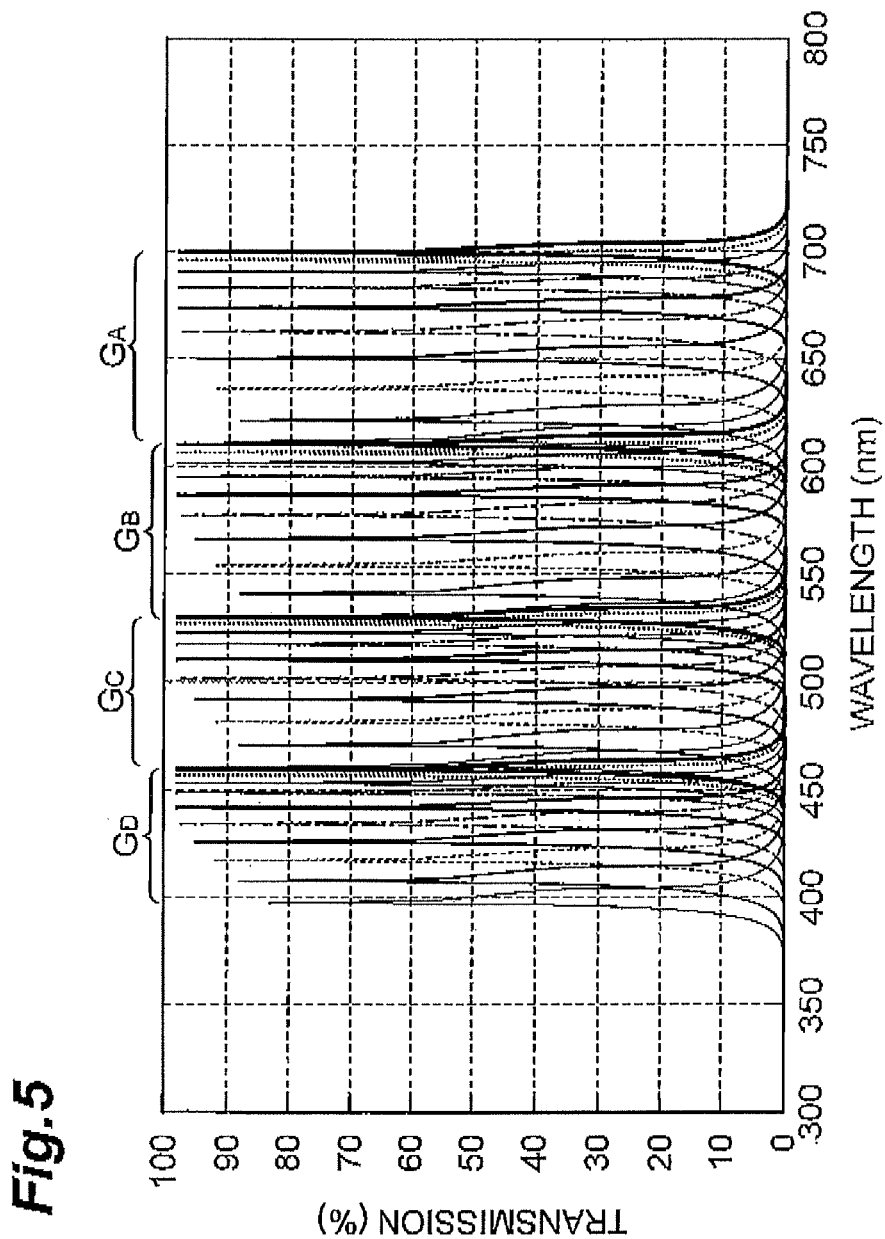
FIG. 5 is a graph showing the wavelength characteristics of light transmissions in the filter rotating body of the light source device of FIG. 1.

FIG. 5 shows the wavelength characteristics of light transmissions in the case where the incident angle to the respective band pass filters 11a to 11d is changed within a range from 0 degrees to 50 degrees in the present embodiment. The characteristics $G_A$, $G_B$, $G_C$, and $G_D$ respectively correspond to the wavelength characteristics of light transmissions corresponding to changes in incident angle to the respective band pass filters 11a, 11b, 11c, and 11d. In this way, it is understood that it is possible to achieve a broad range from approximately 400 nm to 700 nm as a variable range of emission wavelengths of the light source device 1 by controlling the incident angles thereof while switching between the band pass filters 11a to 11d.

According to the light source device 1 described above, the light L2 is made incident along the principal surface 10a of the rotary table 10 from the light source 3, and the light L2 is selectively transmitted through the band pass filters 11a to 11d within a wavelength range according to the incident angle to the band pass filters 11a to 11d, to be output. At this time, by rotating the rotary table 10 centering on the rotational center $C_1$ of the principal surface 10a, it is possible to alternately switch between the four band pass filters 11a to 11d through which the light L2 is transmitted, and it is possible to change the incident angle of the light L2 to the respective band pass filters 11a to 11d within a predetermined angle range, as a result, it is possible to continuously change the emission wavelength.

In particular, provided that the band pass filters 11a to 11d are disposed so that the optical incidence planes 12 are inclined with respect to the lines connecting the rotational center $C_1$ on the principal surface 10a and the center points 15a and 15d of the band pass filters 11a to 11d, the interference among the plurality of band pass filters 11a to 11d is reduced within a range of wide rotation angles (incident angles), as a result, it is possible to easily expand a variable range of emission wavelengths without enlarging the rotary table 10.

Further, because the four band pass filters 11a to 11d are mounted so that the respective lines of intersections formed between the principal surface 10a and the optical incidence planes 12 or the light outgoing planes 13 have contact with the one inscribed circle 17, it is possible to equalize the variable ranges of the incident angles of light to the respective band pass filters 11a to 11d, which makes it possible to efficiently expand the variable range of emission wavelengths with respect to the limited area of the rotary table 10.

Further, because the four band pass filters 11a to 11d are respectively located lateral to the inscribed circle 17 on the principal surface 10a, it is possible to further reduce the interference among the band pass filters 11a to 11d.

Moreover, because the four band pass filters 11a to 11d are disposed so that the lines connecting the rotational center $C_1$ and the center points 15a and 15d of the band pass filters 11a to 11d form angles equal to one another therebetween, so as to be four-fold rotationally symmetric centering on the rotary center $C_1$ on the principal surface 10a, it is possible to equalize the variable ranges of the incident angles of light to the respective band pass filters 11a to 11d, which makes it possible to efficiently expand the variable range of emission wavelengths with respect to the limited area of the rotary table 10.

Figure 17:
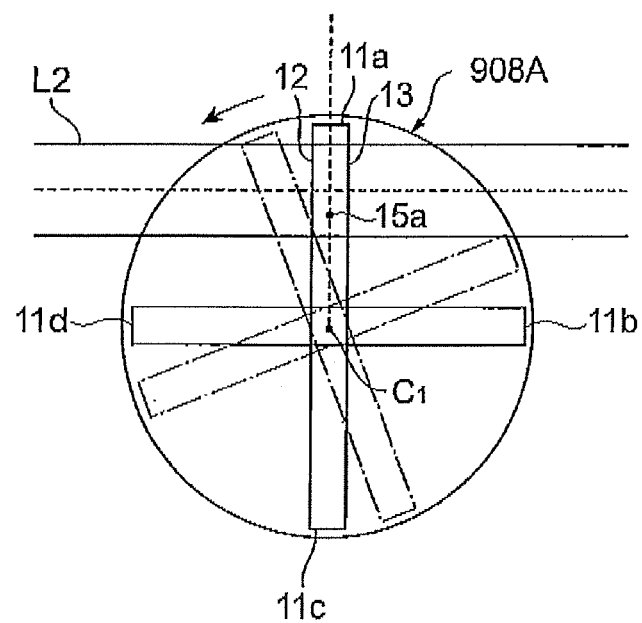
FIG. 17 is a plan view of a filter rotating body as a comparison example of the present invention.
Figure 18:
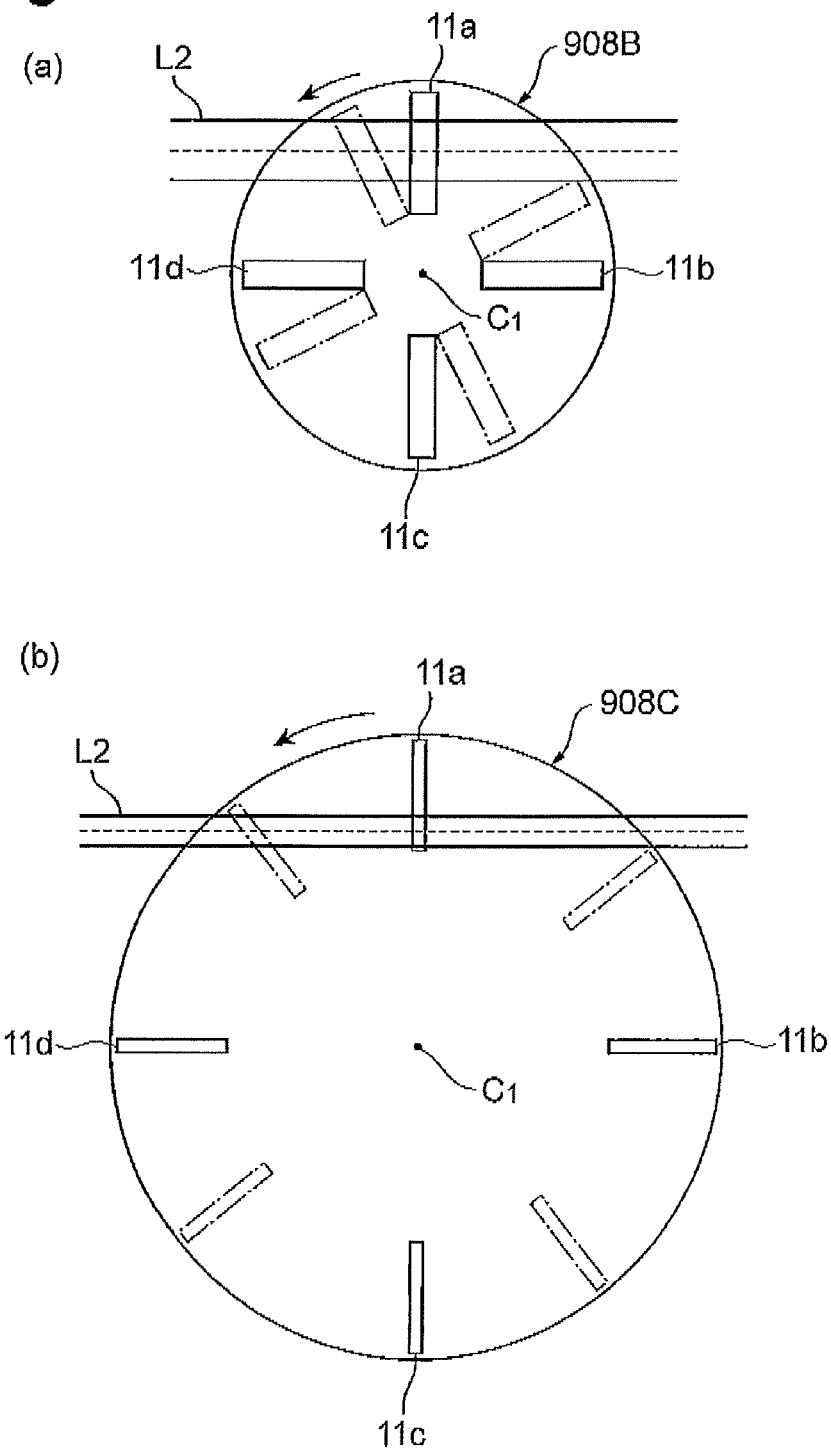
FIG. 18 are plan views of filter rotating bodies as comparison examples of the present invention.

Here, the effect of expansion of the variable range of emission wavelengths according to the present embodiment will be described by comparison with a comparison example. FIGS. 17 and 18 are plan views showing the structures of the filter rotating bodies serving as comparison examples of the present invention.

A filter rotating body 908A shown in FIG. 17 is an example in which the widths and thicknesses of the band pass filters 11a to 11d along the principal surface 10a of the band pass filters 11a to 11d are 10 mm and 2 mm, and the band pass filters 11a to 11d are disposed so that the shortest distance from the rotational center $C_1$ is 1 mm and the incident angle of the optical incidence plane 12 to the lines connecting the rotational center $C_1$ and the center points 15a and 15d is 0 degrees. In the case where this filter rotating body 908A is rotated, in order not to cause interference among the band pass filters 11a to 11d, the variable range of incident angles of the light L2 whose beam diameter is 5 mm is restricted from 0 degrees (the state shown by the solid line in FIG. 17) to 21 degrees (the state shown by the dotted line in FIG. 17).

Further, a filter rotating body 908B shown in FIG. 18B is an example in the case where the shortest distance from the rotational center $C_1$ of the filter rotating body 908A is elongated to 5 mm. In this case, the variable range of incident angles of the light L2 whose beam diameter is 5 mm is from 0 degrees to 27 degrees, that is expanded to a certain extent. However, as compared with the filter rotating body 8 of the present embodiment, it is restricted to a large extent.

Further, a filter rotating body 908C shown in FIG. 18B is an example in which the widths and thicknesses of the band pass filters 11a to 11d are changed to 18 mm and 2 mm, and the shortest distance from the rotational center $C_1$ is elongated to 32 mm with respect to the filter rotating body 908A. In this case, the variable range of incident angles of the light L2 whose beam diameter is 5 mm is from 0 degrees to 39 degrees, which is expanded. However, as compared with the filter rotating body 8 of the present embodiment, this is still narrower. Nevertheless, it is necessary to enlarge the diameter of the rotating table 10 of the filter rotating body 908C to approximately 102 mm to a large extent as compared with the diameter of the rotating table 10 of the filter rotating body 8, that is approximately 30 mm.

In this way, in the case where the band pass filters 11a to 11d are disposed along the lines connecting the rotational center $C_1$ and the center points 15a and 15d, a restriction is placed on an incident angle allocated to each filter due to interference between adjacent filters. Further, because the incident angles to the band pass filters 11a to 11d are within a range of plus and minus angles ranging over 0 degrees (for example, the range of ±21 degrees in the case of the filter rotating body 908A), a practical amount of change in incident angle is an angle which is half the angle variable range. In contrast thereto, in the case of the present embodiment in which the band pass filters 11a to 11d are disposed so as to be inclined with respect to the lines connecting the rotational center $C_1$ and the center points 15a and 15d, it is possible to efficiently expand an incident angle allocated to each filter, and it is possible to effectively utilize the variable range of incident angles thereof, to change a practical incident angle. Moreover, in the case of the present embodiment, it is possible to achieve such an advantage without enlarging the filter rotating body 8.

Here, in FIG. 1, with respect to the wavelength components guided from the wavelength-selective element 7 to the beam damper 9, it is possible to simultaneously output lights with two wavelengths in different wavelength ranges by providing a wavelength-selective mechanism having a similar configuration including a filter rotating body and a rotating mechanism. Further, provided that the wavelength-selective element 7 is made of a half mirror in this case, it is possible to simultaneously output lights with two wavelengths in a same wavelength range. Moreover, in this case, provided that the transmission of the wavelength-selective element 7 is appropriately selected so as to be a plurality of stages, and a wavelength-selective mechanism is provided so as to correspond to those, thereby it is possible to obtain a multiwavelength output.

[Second Embodiment]

Figure 6:
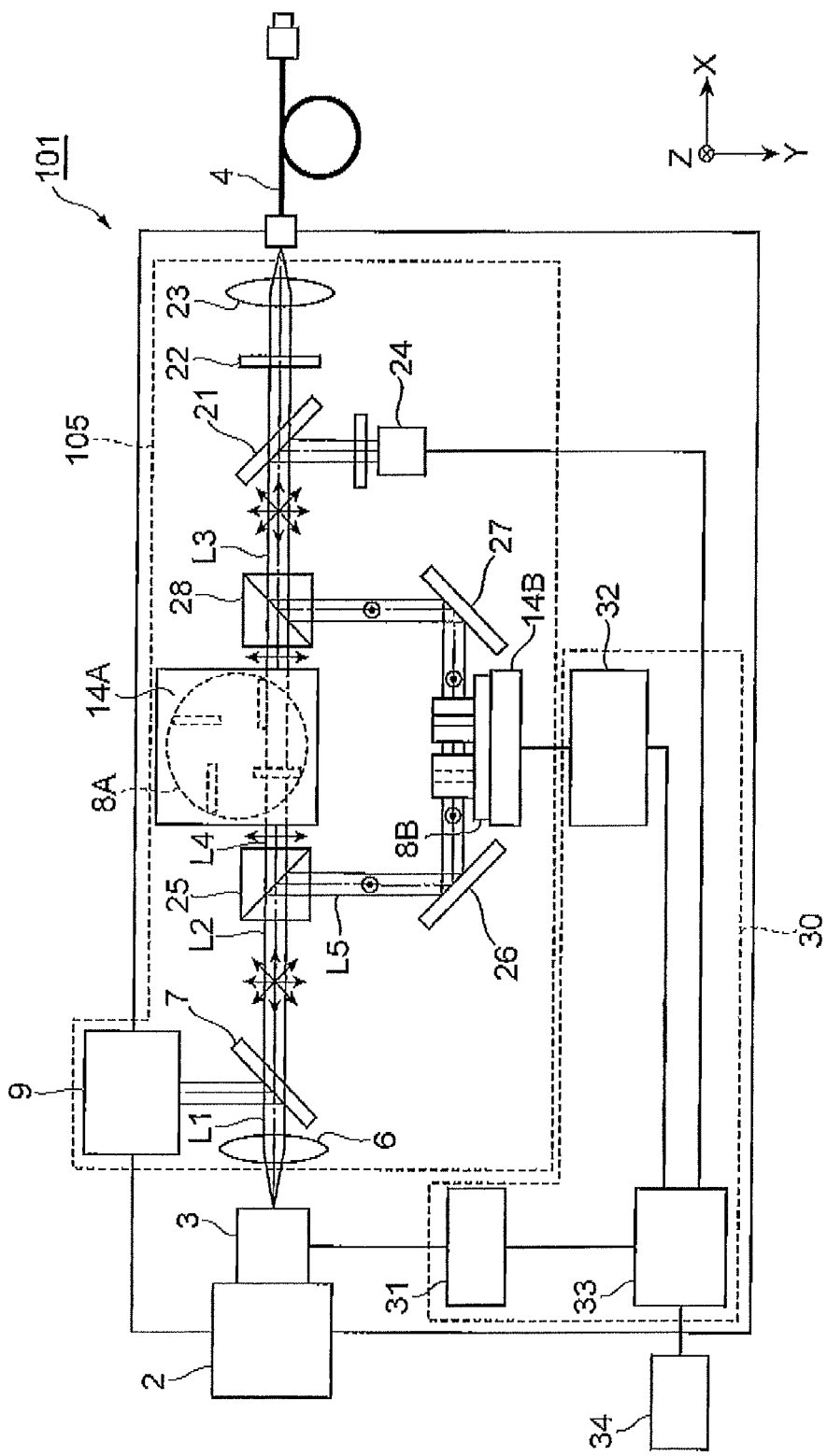
FIG. 6 is a plan view showing a schematic configuration of a light source device according to a second embodiment of the present invention.

Next, a second embodiment of the present invention will be described. FIG. 6 is a plan view showing a schematic configuration of a light source device according to a second embodiment of the present invention. A different point between a light source device 101 shown in the drawing and the light source device 1 according to the first embodiment is that the light source device 101 has a configuration in which two filter rotating bodies 8A and 8B having the same configuration of the filter rotating body 8 are used, and two linearly-polarized components L4 and L5 split from the light L2 are transmitted through the filter rotating bodies 8A and 8B respectively as P polarizations.

In detail, a light conversion optical system 105 of the light source device 101 is provided with a polarization splitter element 25, mirrors 26 and 27, a polarization coupler element 28, the filter rotating bodies 8A and 8B, and rotating mechanisms 14A and 14B for rotating the filter rotating bodies 8A and 8B.

The polarization splitter element 25 is an optical element for receiving the light L2 transmitted through the wavelength-selective element 7, to split the light L2 into two linearly-polarized components perpendicular to one another, and is, for example, a cubic-shaped polarization beam splitter (PBS). In detail, the polarization splitter element 25 splits a polarized component L4 having a polarization direction along the Y axis (hereinafter, called "horizontal polarized component" as well) from the light L2, to cause the polarized component L4 to be transmitted therethrough in the +X axis direction. At the same time, the polarization splitter element 25 splits a polarized component L5 having a polarization direction along the Z axis (hereinafter, called "vertical polarized component" as well) from the light L2, to reflect the polarized component L5 in the +Y axis direction.

The filter rotating bodies 8A and 8B are respectively provided on the optical axes of the polarized components L4 and L5 which are transmitted through or reflected by the polarization splitter element 25. The band pass filters 11a to 11d respectively mounted on these filter rotating bodies 8A and 8B are made uniform in characteristics of the transmissive wavelength ranges to the incident angles of P polarization and S polarization between the two filter rotating bodies 8A and 8B. In more detail, the characteristics of the transmissive wavelength ranges are made uniform between the band pass filters 11a, between the band pass filters 11b, between the band pass filters 11c, and between the band pass filters 11d, which are mounted on the two filter rotating bodies 8A and 8B.

Figure 2:
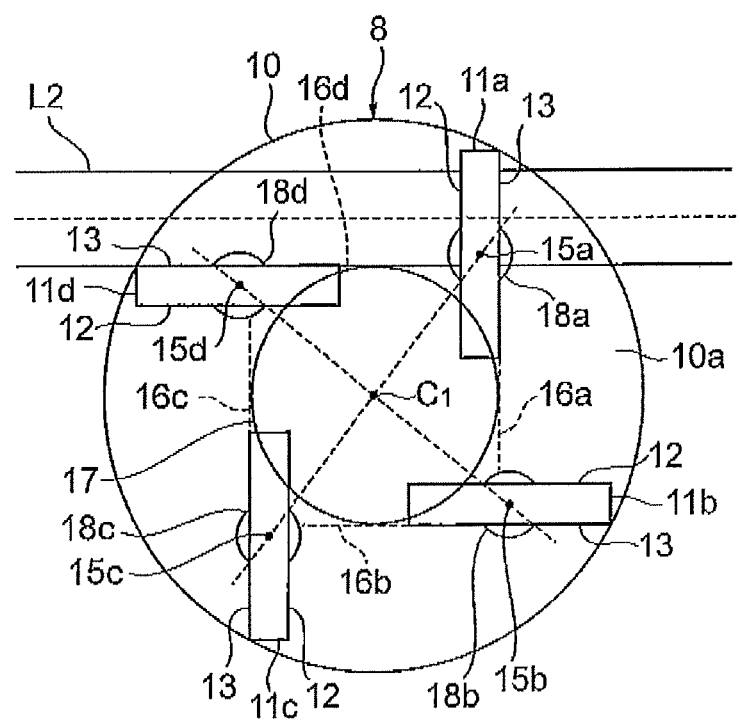
FIG. 2 is a plan view of a filter rotating body of FIG. 1.

The filter rotating body 8A is attached to the rotating mechanism 14A having the rotary shaft along the Z axis so that the principal surface 10a of the rotating table 10 is along the X-Y plane, and is located so that the horizontal polarized component L4 is incident to a space between the rotational center $C_1$ on the principal surface 10a and the peripheral edge portion of the principal surface 10a (refer to FIG. 2). Accordingly, the filter rotating body 8A is capable of changing the incident angle of the horizontal polarized component L4 to the band pass filters 11a to 11d by rotating the rotary table 10, and the horizontal polarized component L4 is incident to the band pass filters 11a to 11d always in a P polarization state.

The filter rotating body 8B is attached to the rotating mechanism 14B having the rotary shaft along the Y axis so that the principal surface 10a of the rotating table 10 is along the Z-X plane, and is located so that the vertical polarized component L5 is incident to a space between the rotational center $C_1$ on the principal surface 10a and the peripheral edge portion of the principal surface 10a (refer to FIG. 2). Further, the mirror 26 that totally-reflects an S-polarized light in an assumed wavelength range is disposed between the polarization splitter element 25 and the filter rotating body 8B, and is configured to reflect the vertical polarized component L5 emitted in the +Y axis direction toward the +X axis direction, to cause the vertical polarized component L5 to be incident to the filter rotating body 8B. Accordingly, the filter rotating body 8B is capable of changing the incident angle of the vertical polarized component L5 to the band pass filters 11a to 11d by rotating the rotary table 10, and the vertical polarized component L5 is incident to the band pass filters 11a to 11d always in a P polarization state.

Here, the rotary shaft of the rotary table 10 becomes perpendicular between the filter rotating body 8A and the filter rotating body 8B so that the vertical polarized component L5 is incident to the band pass filters 11a to 11d as a P polarization. Meanwhile, the rotary shaft of the rotary table 10 is in the same direction, and the vertical polarized component L5 may be made incident to the band pass filters 11a to 11d as a P polarization by rotating the polarization plane by use of λ/2 plates or the like. In addition, as places where the λ/2 plates are used, the λ/2 plates are inserted in front and back of the band pass filters.

The polarization coupler element 28 is disposed in the +X axis direction along the optical axis of the horizontal polarized component L4 transmitted through the filter rotating body 8A, and the mirror 27 is disposed between the polarization coupler element 28 and the filter rotating body 8B. The mirror 27 serves to totally reflect an S polarization in an assumed wavelength range, and reflect the vertical polarized component L5 transmitted through the filter rotating body 8B, to cause the vertical polarized component L5 to be incident to the polarization coupler element 28 in the Y axis direction.

This polarization coupler element 28 is an optical element for coupling the two polarized components L4 and L5 perpendicular to one another into one, and for example, a cubic-shaped polarization beam splitter (PBS) is used. In detail, the polarization coupler element 28 synthesizes the horizontal polarized component L4 incident along the X axis and the vertical polarized component L5 incident along the Y axis, to generate synthesized light L3 in an unpolarized state, to emit the synthesized light L3 in the +X axis direction. The synthesized light L3 synthesized by the polarization coupler element 28 is partially guided by the power monitor 24, and is simultaneously guided to the optical fiber 4 via the beam sampler 21, the shutter 22, and the condenser lens 23, to be irradiated to the outside.

The control circuit 33 of the control system 30 controls the rotating mechanisms 14A and 14B and changes their rotating angles so that the respective polarized components L4 and L5 are incident to any one of the band pass filter 11 a, the band pass filter 11b, the band pass filter 11 c, and the band pass filter 11d having the same light transmission characteristics which are mounted on the filter rotating bodies 8A and 8B, and the incident angles of the polarized components L4 and L5 to the band pass filters 11 a to 11 d are made uniform. In this way, provided that the incident angles of the two polarized components L4 and L5 are made uniform, the filter rotating bodies 8A and 8B are disposed so that the polarized components L4 and L5 corresponding to the respective incident angles are matched to one another. That is, the polarized components L4 and L5 after being transmitted through the filter rotating bodies 8A and 8B have the same spectrum profile.

According to the light source device 101, after the horizontal polarized component L4 split by the polarization splitter element 25 is made incident to the filter rotating body 8A as a P polarization, and the vertical polarized component L5 split by the polarization splitter element 25 is made incident to the filter rotating body 8B as a P polarization at the same incident angle as that of the horizontal polarized component L4, the lights transmitted through the two filter rotating bodies 8A and 8B are coupled to be emitted to the outside. Here, because the characteristics of the transmissive wavelength ranges with respect to the incident angles of the P polarizations to the band pass filters 11a to 11d mounted on the two filter rotating bodies 8A and 8B are made uniform, provided that the incident angles are appropriately set, it is possible to narrow and stabilize the range of the emission characteristics over the assumed wavelength range, and it is possible to efficiently utilize the light from the light source to emit the light.

Further, provided that the incident angles of the two polarized components L4 and L5 to the band pass filters 11a to 11d are set to different angles, it is possible to simultaneously obtain two different wavelength outputs. In this case, the polarization directions of the two wavelength outputs are a vertical polarization and a horizontal polarization, which are perpendicular to one another. Meanwhile, the two wavelength outputs may be brought into an unpolarized state by use of depolarization plates or the like.

Figure 7:
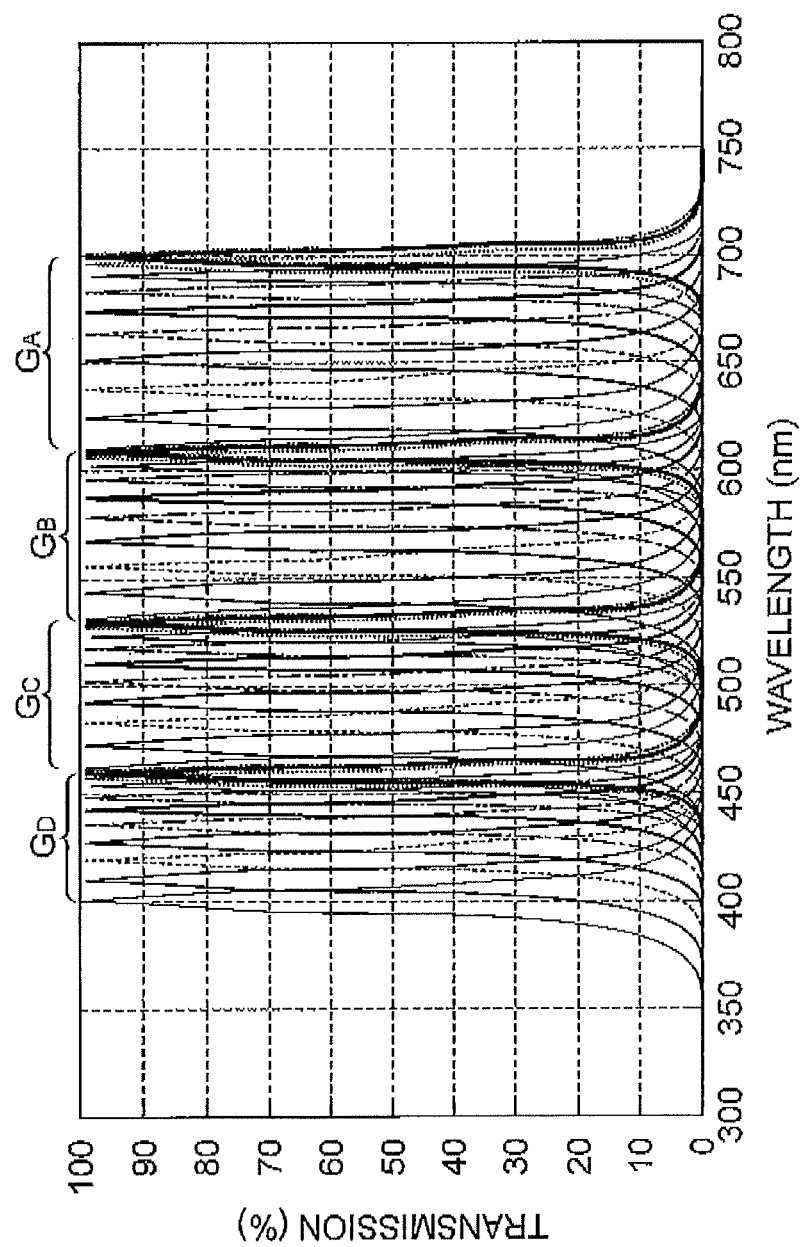
FIG. 7 is a graph showing the wavelength characteristics of light transmissions in two filter rotating bodies of the light source device of FIG. 6.

FIG. 7 shows the wavelength characteristics of light transmissions in the case where the incident angles to the band pass filters 11a to 11d of the two filter rotating bodies 8A and 8B are changed within a range from 0 degrees to 50 degrees in the present embodiment. In this way, it is understood that light from the light source 3 is split into two linearly-polarized components and the incident angles of the respective components to the band pass filters 11a to 11d are controlled, to be able to stabilize the emission intensity characteristics in a broad variable wavelength range.

[Third Embodiment]

Figure 8:
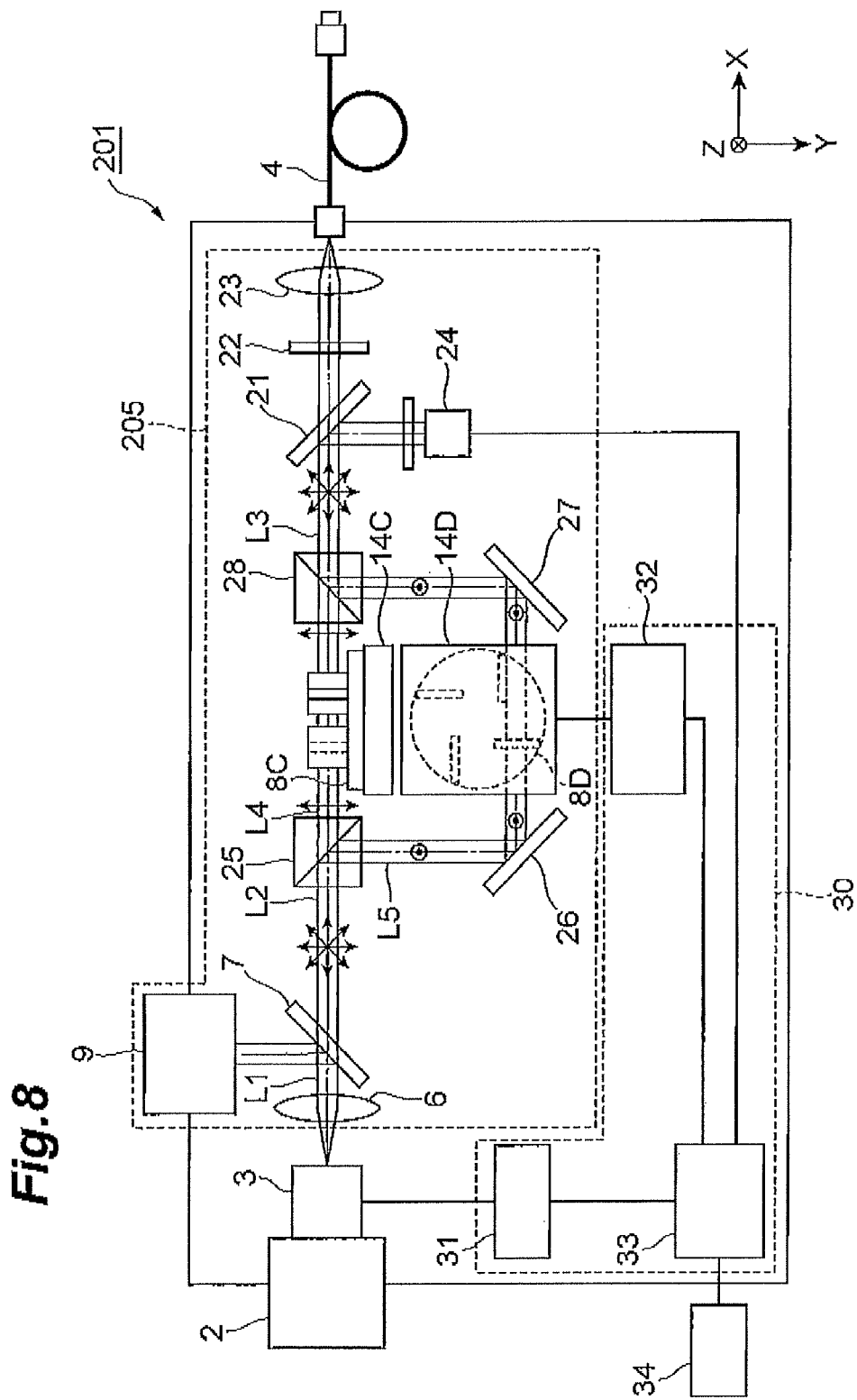
FIG. 8 is a plan view showing a schematic configuration of a light source device according to a third embodiment of the present invention.

FIG. 8 is a plan view showing a schematic configuration of a light source device according to a third embodiment of the present invention. A different point between a light source device 201 shown in the drawing and the light source device 101 according to the second embodiment is that the light source device 201 has a configuration in which the polarized components L4 and L5 are transmitted through two rotating bodies 8C and 8D respectively as S polarizations.

The filter rotating body 8C is attached to a rotating mechanism 14C having the rotary shaft along the Y axis so that the principal surface 10a of the rotating table 10 is along the Z-X plane, and is located so that the horizontal polarized component L4 is incident to a space between the rotational center $C_1$ on the principal surface 10a and the peripheral edge portion of the principal surface 10a (refer to FIG. 2). Accordingly, the filter rotating body 8C is capable of changing the incident angle of the horizontal polarized component L4 to the band pass filters 1a to 11d by rotating the rotary table 10, and the horizontal polarized component L4 is incident to the band pass filters 11a to 11d always in an S polarization state.

The filter rotating body 8D is attached to a rotating mechanism 14D having the rotary shaft along the Z axis so that the principal surface 10a of the rotating table 10 is along the X-Y plane, and is located so that the vertical polarized component L5 is incident to a space between the rotational center $C_1$ on the principal surface 10a and the peripheral edge portion of the principal surface 10a (refer to FIG. 2).

Accordingly, the filter rotating body 8D is capable of changing the incident angle of the vertical polarized component L5 to the band pass filters 11a to 11d by rotating the rotary table 10, and the vertical polarized component L5 is incident to the band pass filters 11a to 11d always in an S polarization state.

Here, the rotary shaft of the rotary table 10 becomes perpendicular between the filter rotating body 8C and the filter rotating body 8D so that the vertical polarized component L5 is incident to the band pass filters 11a to 11d as an S polarization. Meanwhile, the rotary shaft of the rotary table 10 is in the same direction, and the vertical polarized component L5 may be made incident to the band pass filters 11a to 11d as an S polarization by rotating the polarization plane by use of λ/2 plates or the like. In addition, as places where the λ/2 plates are used, the λ/2 plates are inserted in front and back of the band pass filters.

The control circuit 33 of the control system 30 controls the rotating mechanisms 14C and 14D and changes their rotating angles so that the respective polarized components L4 and L5 are incident to any one of the band pass filter 11a, the band pass filter 11b, the band pass filter 11c, and the band pass filter 11d having the same light transmission characteristics, which are mounted on the filter rotating bodies 8C and 8D, and the incident angles of the polarized components L4 and L5 to the band pass filters 11a to 11d are made uniform.

In accordance with the light source device 201, after the horizontal polarized component L4 split by the polarization splitter element 25 is made incident to the filter rotating body 8C as an S polarization, and the vertical polarized component L5 split by the polarization splitter element 25 is made incident to the filter rotating body 8D as an S polarization at the same incident angle as that of the horizontal polarized component L4, the lights transmitted through the two filter rotating bodies 8C and 8D are coupled to be emitted to the outside. Here, because the characteristics of the transmissive wavelength ranges with respect to the incident angles of the S polarizations to the band pass filters 11a to 11d mounted on the two filter rotating bodies 8C and 8D are made uniform, provided that the incident angles are appropriately set, it is possible to narrow and stabilize the range of the emission characteristics over the assumed wavelength range, and it is possible to efficiently utilize the light from the light source to emit the light.

Further, provided that the incident angles of the two polarized components L4 and L5 to the band pass filters 11a to 11d are set to different angles, it is possible to simultaneously obtain two different wavelength outputs. In this case, the polarization directions of the two wavelength outputs are a vertical polarization and a horizontal polarization, which are perpendicular to one another. Meanwhile, the two wavelength outputs may be brought into an unpolarized state by use of depolarization plates or the like.

Figure 9:
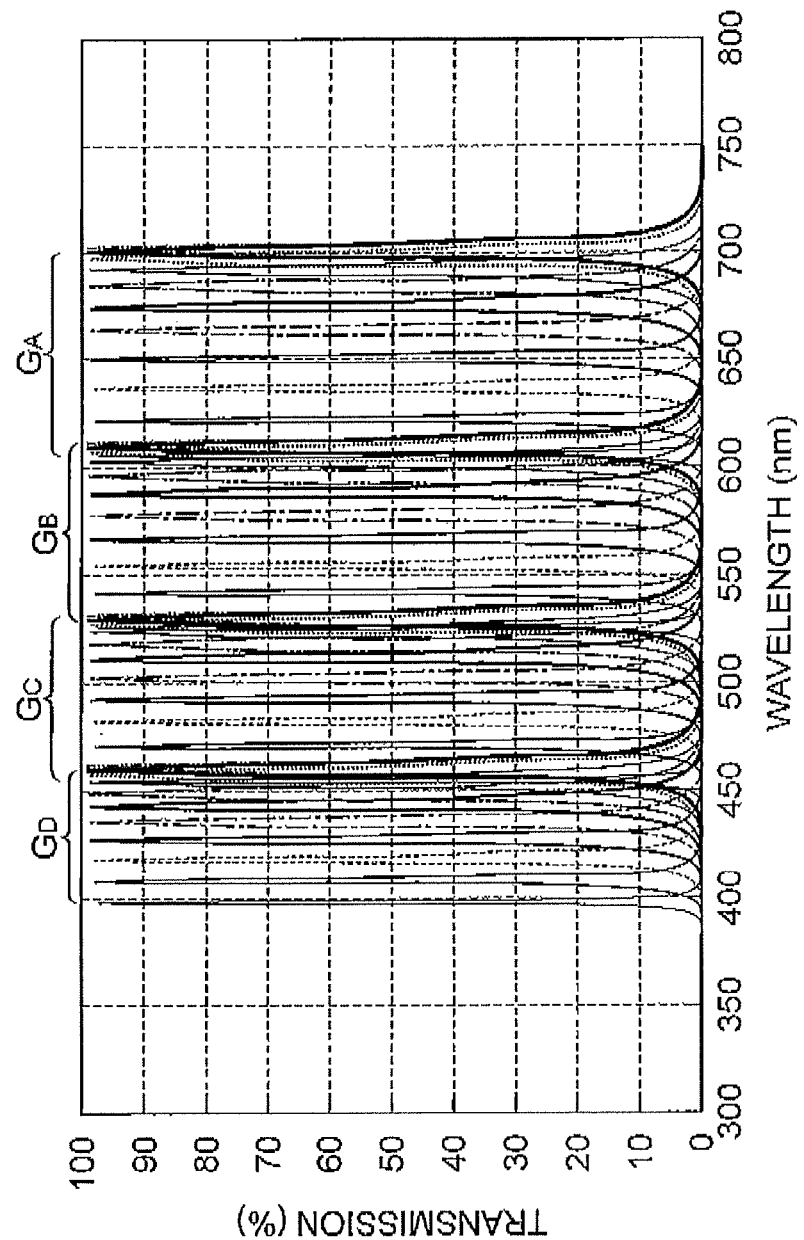
FIG. 9 is a graph showing the wavelength characteristics of light transmissions in two filter rotating bodies of the light source device of FIG. 8.

FIG. 9 shows the wavelength characteristics of light transmissions in the case where the incident angles to the band pass filters 11a to 11d of the two filter rotating bodies 8C and 8D are changed within a range from 0 degrees to 50 degrees in the present embodiment. In this case as well, it is understood that light from the light source 3 is split into two linearly-polarized components and the incident angles of the respective components to the band pass filters 11a to 11d are controlled, to be able to stabilize the emission intensity characteristics in a broad variable wavelength range.

In addition, the present invention is not limited to the aforementioned embodiments. For example, the number of band pass filters mounted on the filter rotating body 8 is not limited to a specific number, and an arbitrary number greater than or equal to 3 may be selected according to an assumed wavelength range and an area of the filter rotating body 8.

Figure 10:
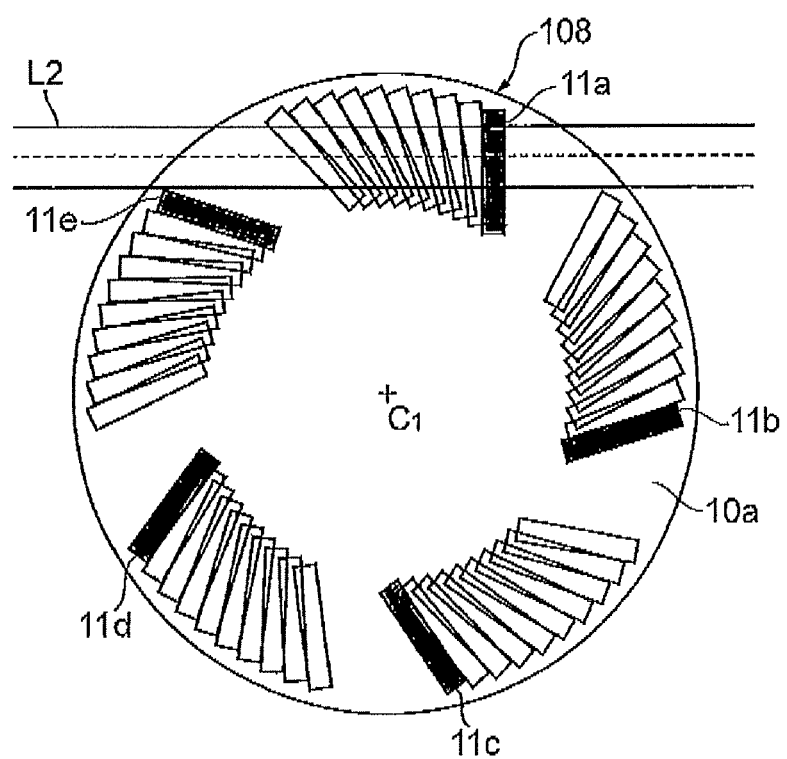
FIG. 10 is a plan view of a filter rotating body as a modified example of the present invention.

FIG. 10 shows the structure of a filter rotating body 108 having five band pass filters 11*a* to 11*e*. In this case, a beam diameter of the light L2 is 5 mm, the widths and thicknesses along the principal surface 10*a* of the band pass filters 11*a* to 11*e* are 10 mm and 2 mm, and the shortest distance $R_1$ from the rotational center $C_1$ to the band pass filters 11*a* to 11*e* is 15.3 mm, and when the band pass filters 11*a* to 11*e* are rotated in a counterclockwise direction, the variable range of incident angles to each of the band pass filters 11*a* to 11*e* is set to 0 degrees to 45 degrees.

Figure 11:
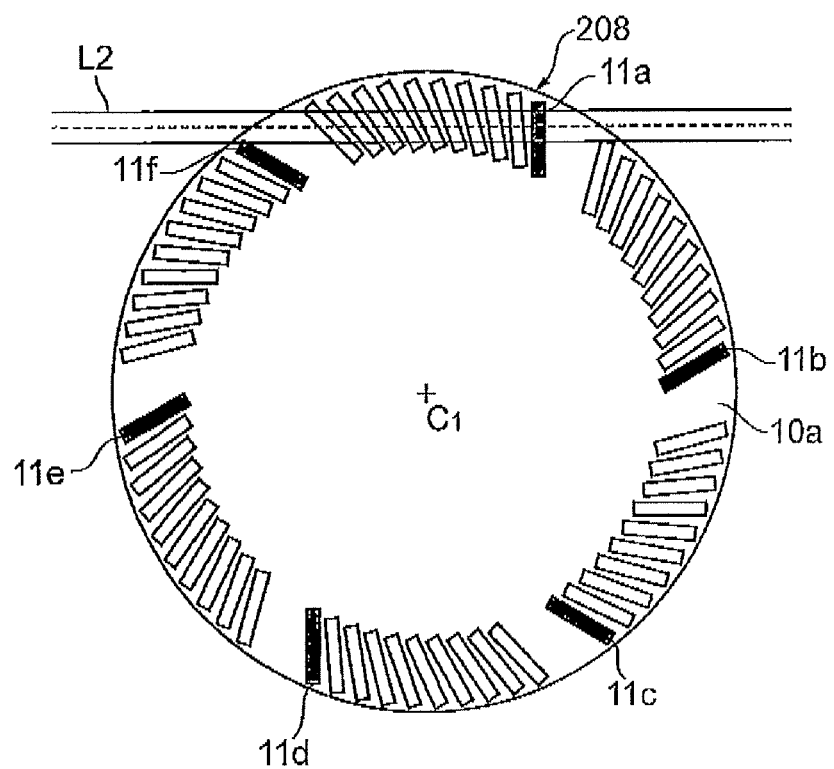
FIG. 11 is a plan view of a filter rotating body as a modified example of the present invention.

Further, FIG. 11 shows the structure of a filter rotating body 208 having six band pass filters 11*a* to 11*f*. In this case, a beam diameter of the light L2 is 5 mm, the widths and thicknesses along the principal surface 10*a* of the band pass filters 11*a* to 11*f* are 12 mm and 2 mm, and the shortest distance $R_1$ from the rotational center $C_1$ to the band pass filters 11*a* to 11*f* is 39.4 mm, and when the band pass filters 11*a* to 11*f* are rotated in a counterclockwise direction, the variable range of incident angles to each of the band pass filters 11*a* to 11*f* is set to 0 degrees to 45 degrees.

Figure 12:
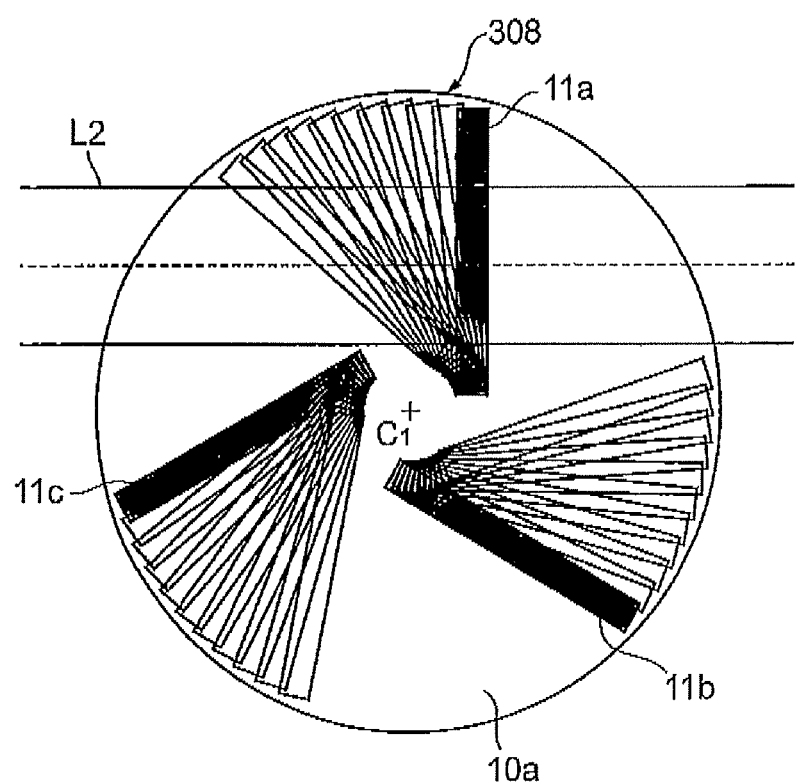
FIG. 12 is a plan view of a filter rotating body as a modified example of the present invention.

Further, FIG. 12 shows the structure of a filter rotating body 308 having three band pass filters 11*a* to 11*c*. In this case, a beam diameter of the light L2 is 10 mm, the widths and thicknesses along the principal surface 10*a* of the band pass filters 11*a* to 11*c* are 18 mm and 2 mm, and the shortest distance $R_1$ from the rotational center $C_1$ to the band pass filters 11*a* to 11*c* is 3.16 mm, and when the band pass filters 11*a* to 11*c* are rotated in a counterclockwise direction, the variable range of incident angles to each of the band pass filters 11*a* to 11*c* is set to 0 degrees to 50 degrees.

Figure 19:
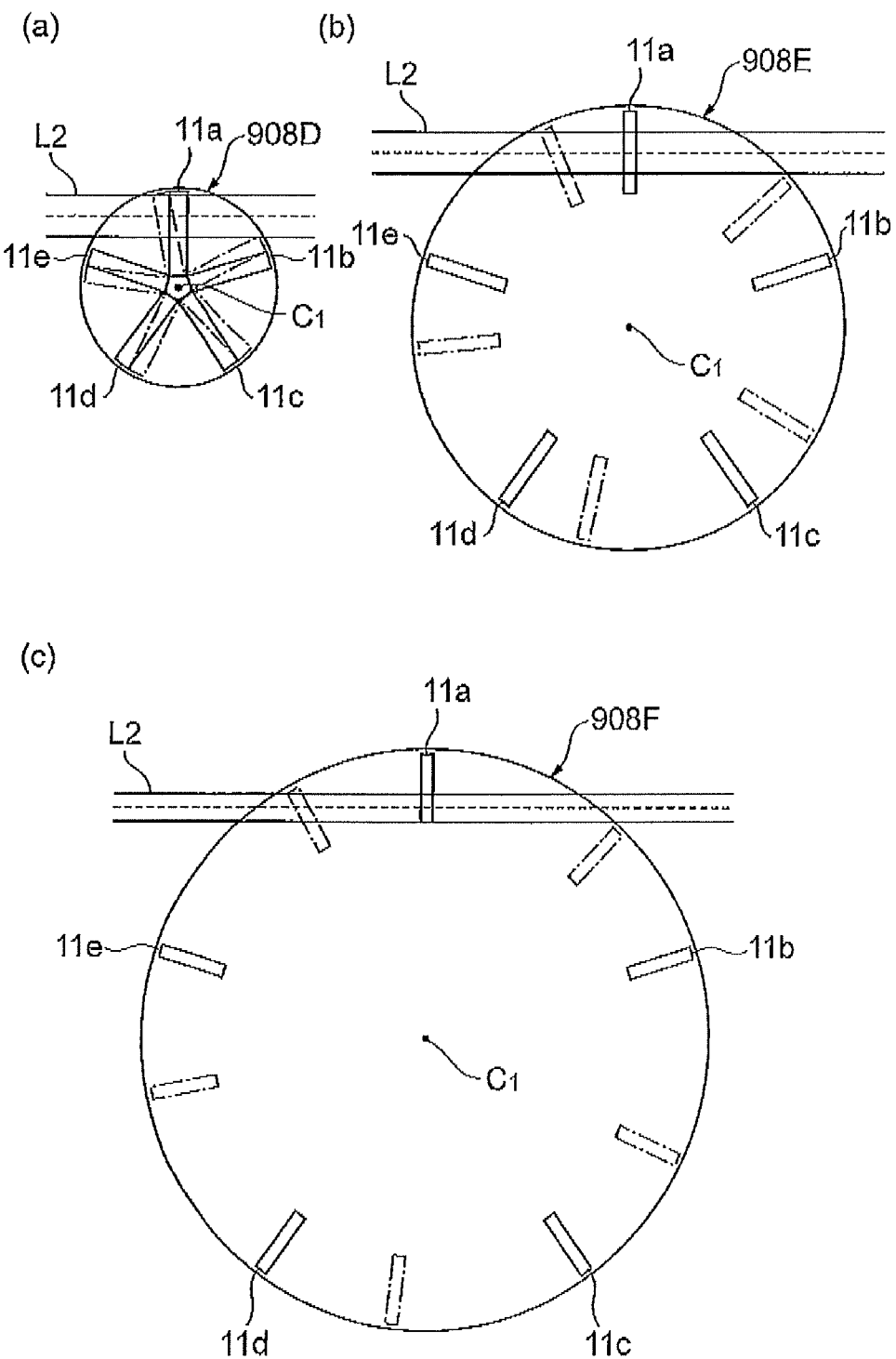
FIG. 19 are plan views of filter rotating bodies as comparison examples of the present invention.

In contrast thereto, a filter rotating body 908D shown in FIG. 19A as a comparison example of the present invention is an example in which the widths and thicknesses along the principal surface 10*a* of the band pass filters 11*a* to 11*e* are 10 mm and 2 mm, and the band pass filters 11*a* to 11*e* are disposed so that the shortest distance from the rotational center $C_1$ is 1.38 mm and the inclination angles of the optical incidence planes to the lines connecting the rotational center $C_1$ and the center points of the band pass filters 11*a* to 11*e* are 0 degrees. In the case where this filter rotating body 908D is rotated, in order not to cause interference among the band pass filters 11*a* to 11*e*, the variable range of incident angles of the light L2 whose beam diameter is 5 mm is restricted from 0 degrees to 9 degrees. Further, a filter rotating body 908E shown in FIG. 19B as a comparison example of the present invention is an example in which the widths and thicknesses along the principal surface 10*a* of the band pass filters 11*a* to 11*e* are 10 mm and 2 mm, and the band pass filters 11*a* to 11*e* are disposed so that the shortest distance from the rotational center $C_1$ is 16.38 mm and the inclination angles of the optical incidence planes to the lines connecting the rotational center $C_1$ and the center points of the band pass filters 11*a* to 11*e* are 0 degrees. In the case where this filter rotating body 908E is rotated, the variable range of incident angles of the light L2 whose beam diameter is 5 mm is restricted from 0 degrees to 24 degrees. Moreover, a filter rotating body 908F shown in FIG. 19C as a comparison example of the present invention is an example in which the widths and thicknesses along the principal surface 10*a* of the band pass filters 11*a* to 11*e* are 12 mm and 2 mm, and the band pass filters 11*a* to 11*e* are disposed so that the shortest distance from the rotational center $C_1$ is 32 mm and the inclination angles of the optical incidence planes to the lines connecting the rotational center $C_1$ and the center points of the band pass filters 11*a* to 11*e* are 0 degrees. In the case where this filter rotating body 908F is rotated, regardless of the fact that the diameter of the rotary table 10 is increased, the variable range of incident angles of the light L2 whose beam diameter is 5 mm is restricted from 0 degrees to 29 degrees. In this way, as compared with the filter rotating body 108 of FIG. 10 using the same number of band pass filters, the variable range of incident angles is restricted to a large extent.

Figure 20:
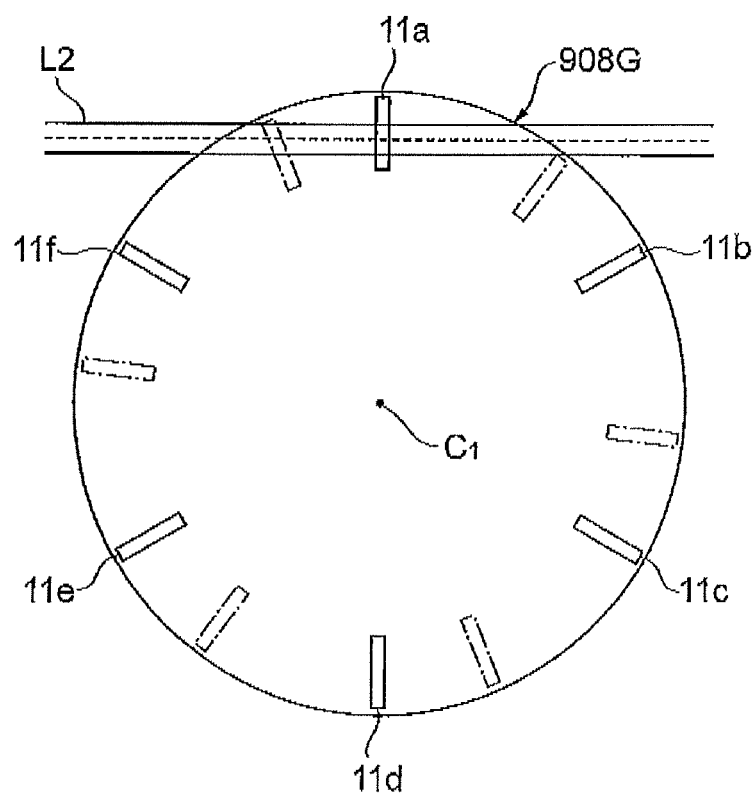
FIG. 20 is a plan view of a filter rotating body as a comparison example of the present invention.

Further, a filter rotating body 908G shown in FIG. 20 as a comparison example of the present invention is an example in which the widths and thicknesses along the principal surface 10*a* of the band pass filters 11*a* to 11*f* are 12 mm and 2 mm, and the band pass filters 11*a* to 11*f* are disposed so that the shortest distance from the rotational center $C_1$ is 32 mm, and the inclination angles of the optical incidence planes to the lines connecting the rotational center $C_1$ and the center points of the band pass filters 11*a* to 11*f* are 0 degrees. In the case where this filter rotating body 908G is rotated, the variable range of incident angles of the light L2 whose beam diameter is 5 mm is restricted from 0 degrees to 23 degrees. In this way, as compared with the filter rotating body 208 of FIG. 11 using the same number of band pass filters, the variable range of incident angles is restricted to a large extent.

Figure 21:
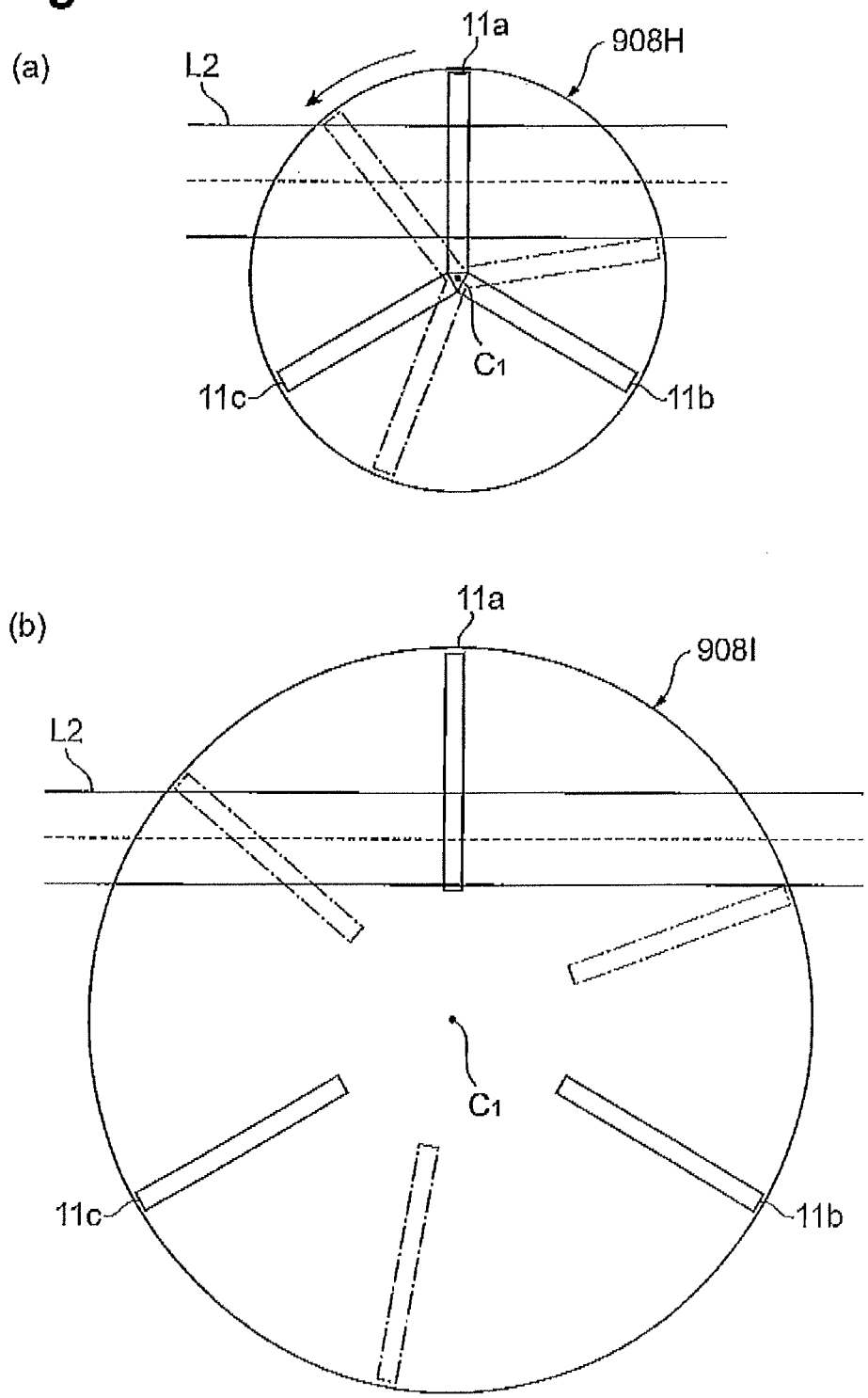
FIG. 21 are plan views of filter rotating bodies as comparison examples of the present invention.

Further, a filter rotating body 908H shown in FIG. 21A as a comparison example of the present invention is an example in which the widths and thicknesses along the principal surface 10*a* of the band pass filters 11*a* to 11*c* are 18 mm and 2 mm, and the band pass filters 11*a* to 11*c* are disposed so that the shortest distance from the rotational center $C_1$ is 0.577 mm, and the inclination angles of the optical incidence planes to the lines connecting the rotational center $C_1$ and the center points of the band pass filters 11*a* to 11*c* are 0 degrees. In the case where this filter rotating body 908H is rotated, the variable range of incident angles of the light L2 whose beam diameter is 10 mm is restricted from 0 degrees to 38 degrees, and as compared with the filter rotating body 308 of FIG. 12, the variable range of incident angles is restricted to a large extent. Further, a filter rotating body 908I shown in FIG. 21B as a comparison example of the present invention is an example in which the widths and thicknesses along the principal surface 10*a* of the band pass filters 11*a* to 11*c* are 26 mm and 2 mm, and the band pass filters 11*a* to 11*c* are disposed so that the shortest distance from the rotational center $C_1$ is 14.577 mm, and the inclination angles of the optical incidence planes to the lines connecting the rotational center $C_1$ and the center points of the band pass filters 11*a* to 11*c* are 0 degrees. In the case where this filter rotating body 908I is rotated, the variable range of incident angles of the light L2 whose beam diameter is 10 mm is from 0 degrees to 50 degrees. Meanwhile, as compared with the filter rotating body 308 of FIG. 12, the diameter of the rotary table 10 is increased more than double.

The variable range of incident angles to the band pass filters 11*a* to 11*d* of the filter rotating body 8 may be set to various ranges by changing the inclination angles of the band pass filters 11*a* to 11*d*.

Figure 13:
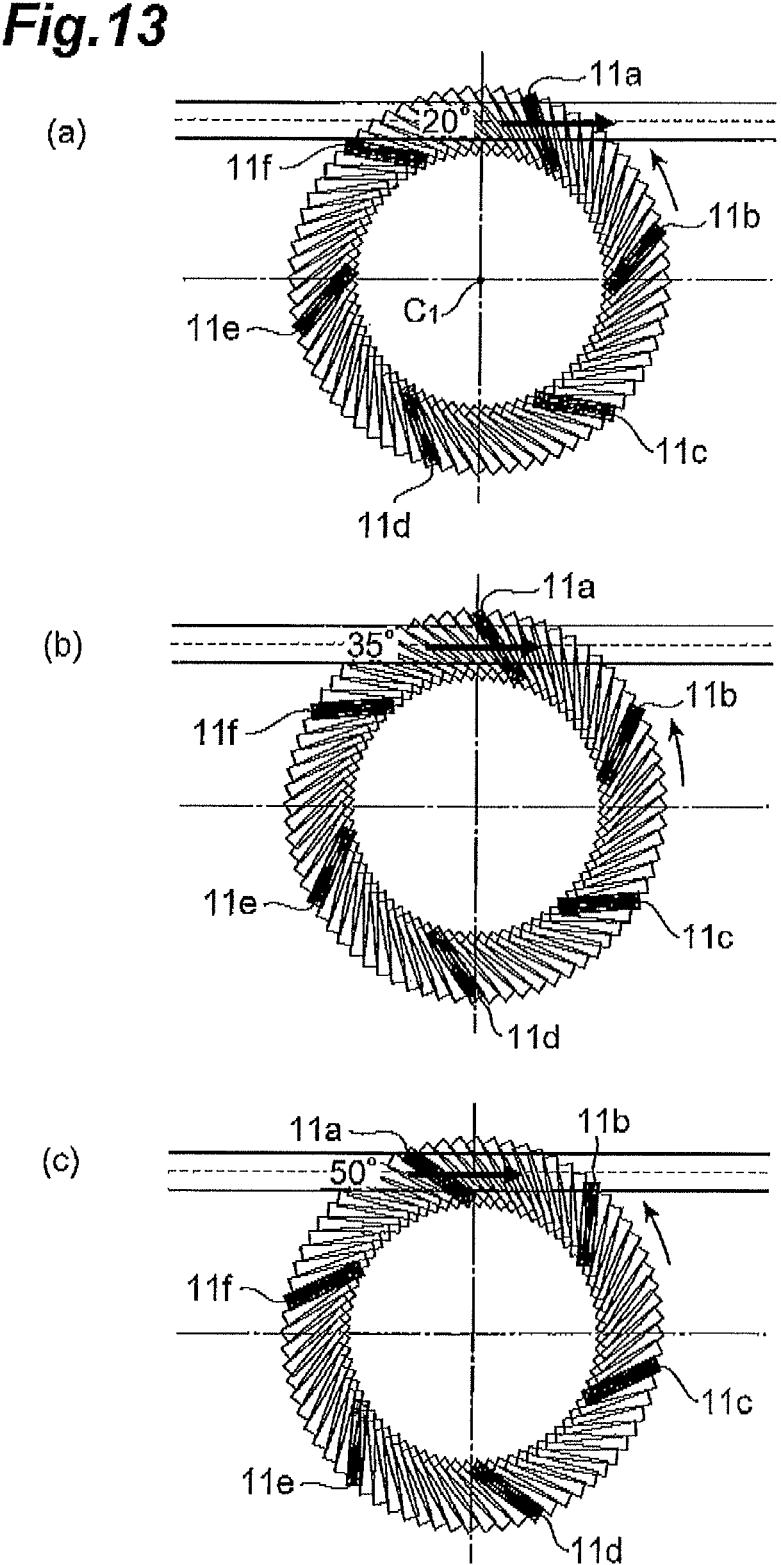
FIG. 13 are plan views of a filter rotating body as a modified example of the present invention.
Figure 14:
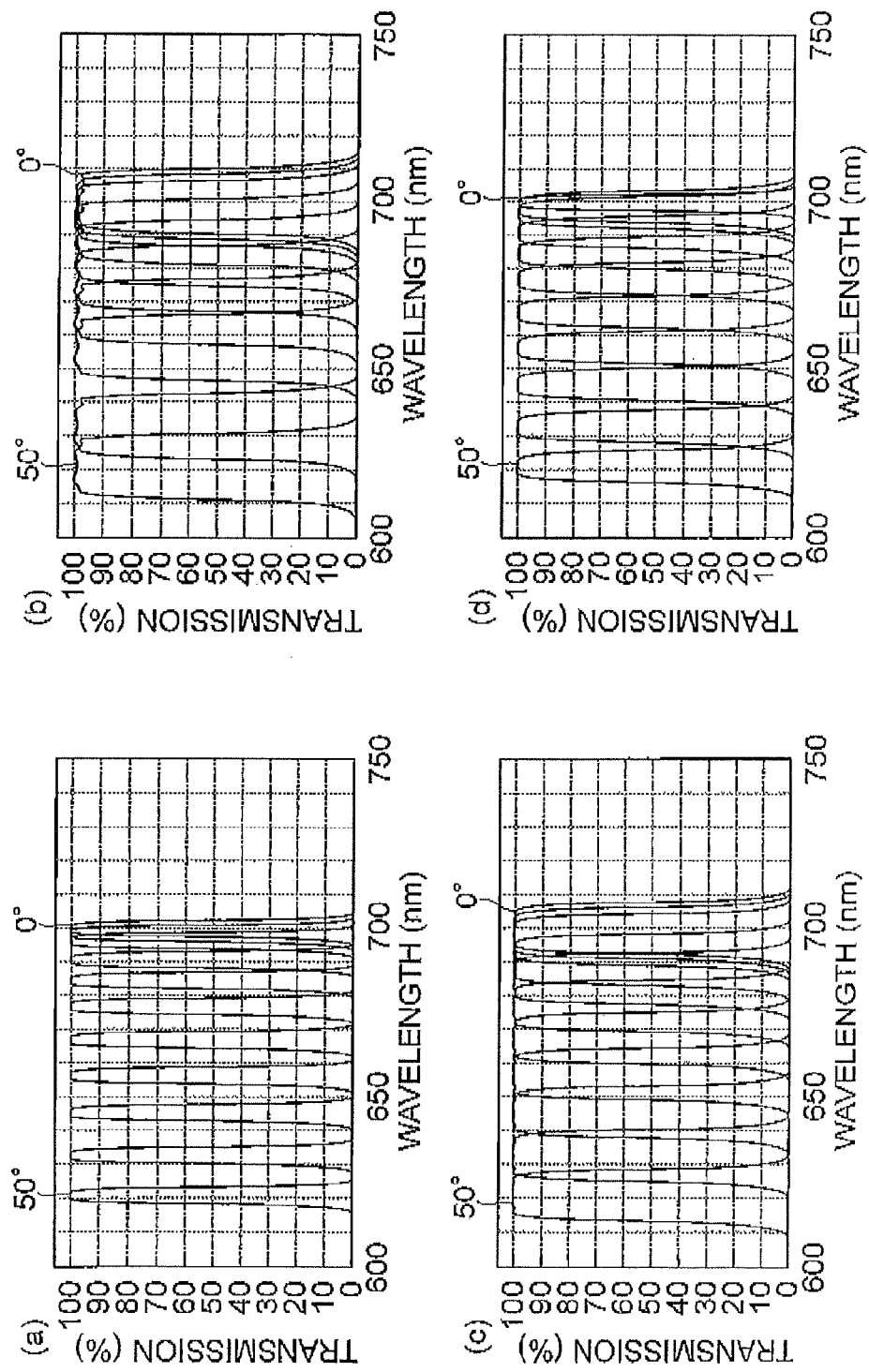
FIG. 14 are graphs showing the characteristics of the transmissive wavelength ranges of the band pass filters as a modified example of the present invention.

For example, the minimum angle included in the variable range of incident angles is not limited to 0 degrees. In detail, as shown in FIG. 13, the band pass filters 11*a* to 11*f* may be disposed so that the inclination angles of the optical incidence planes to the lines connecting the rotational center $C_1$ on the principal surface 10*a* and the center points of the band pass filters 11*a* to 11*f* are increased, and the variable range of incident angles to the band pass filters 11*a* to 11*f* are set, for example, from 20 degrees to 50 degrees. The drawings show an example in which the widths and thicknesses along the principal surface 10a of the band pass filters 11a to 11f are 11 mm and 2 mm, the band pass filters 11a to 11f are set so that the shortest distance from the rotational center $C_1$ is 16.6 mm, and the beam diameter of the light L2 is set to 5 mm. In this way, provided that the minimum angle included in the variable range of incident angles is set to be greater than 0 degrees, it is possible to increase a change of the transmissive wavelength range to a change in incident angle, which makes it possible to considerably expand the total wavelength-variable range. For example, in the case of the band pass filter 11a having incident angle dependence of a peak wavelength in the transmissive wavelength range as shown in FIG. 3, when the incident angle is changed within a range from 0 degrees to 30 degrees, the variation width of peak wavelengths is 5.43% with respect to the maximum peak wavelength. In contrast thereto, it is understood that, when the incident angle to the band pass filter 11a is changed within a range from 20 degrees to 50 degrees, the variation width of peak wavelengths is 11.18%, which makes it possible to have a large change of the transmissive wavelength range by the same change in incident angle.

Further, the band pass filters 11a to 11d built-in the light source devices 1, 101, and 201 of the present embodiment respectively have different central wavelengths in the transmissive wavelength ranges with respect to the same incident angle. However, those may be configured to have the same central wavelength and different half bandwidths. FIGS. 14A to 14D respectively show examples of the characteristics of the transmissive wavelength ranges in the case where the incident angles are changed within a range from 0 degrees to 50 degrees in the band pass filters 11a to 11d. In this way, in the case where the band pass filters 11a to 11d having the same central wavelength are used, it is possible to easily expand the variable range of selective wavelengths while switching the band width.

Figure 15:
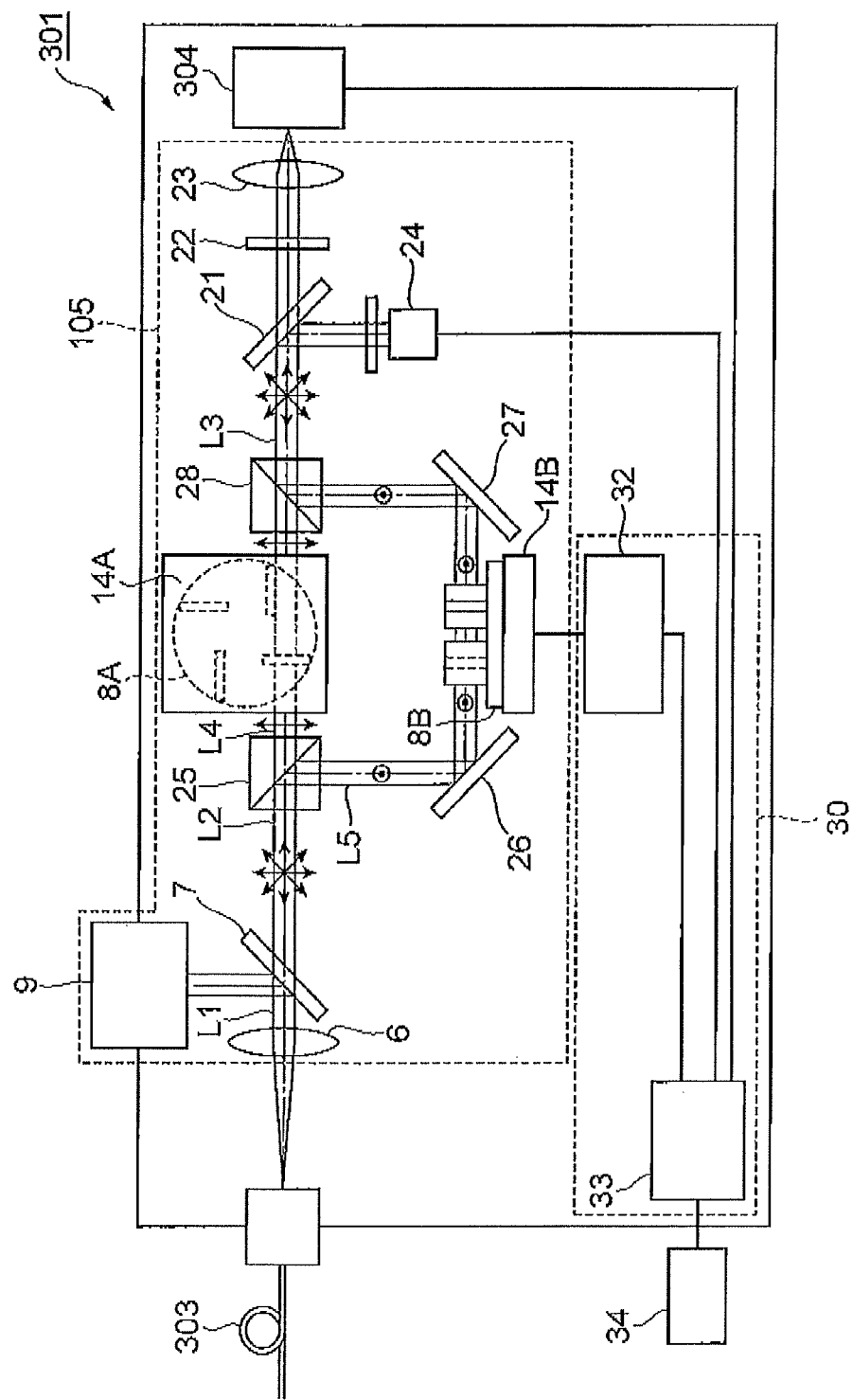
FIG. 15 is a plan view showing a schematic configuration of a light detection device according to another embodiment of the present invention.

As an embodiment of a spectral device of the present invention, other than the light source devices described above, a light detection device 301 as shown in FIG. 15 may be cited. This light detection device 301 is a device for spectroscopically detecting a predetermined wavelength component in light input from the outside, and includes a light conversion optical system 105 having the same configuration as the light source device 101, an optical fiber 303 guiding the light from the outside to the collimator lens 6, and a photodetector 304 detecting the spectroscopic light by the light conversion optical system 105. According to the light detection device 301 as well, it is possible to easily expand a variable range of detection wavelengths without enlarging the device at the time of spectroscopically detecting light from the outside.

Figure 16:
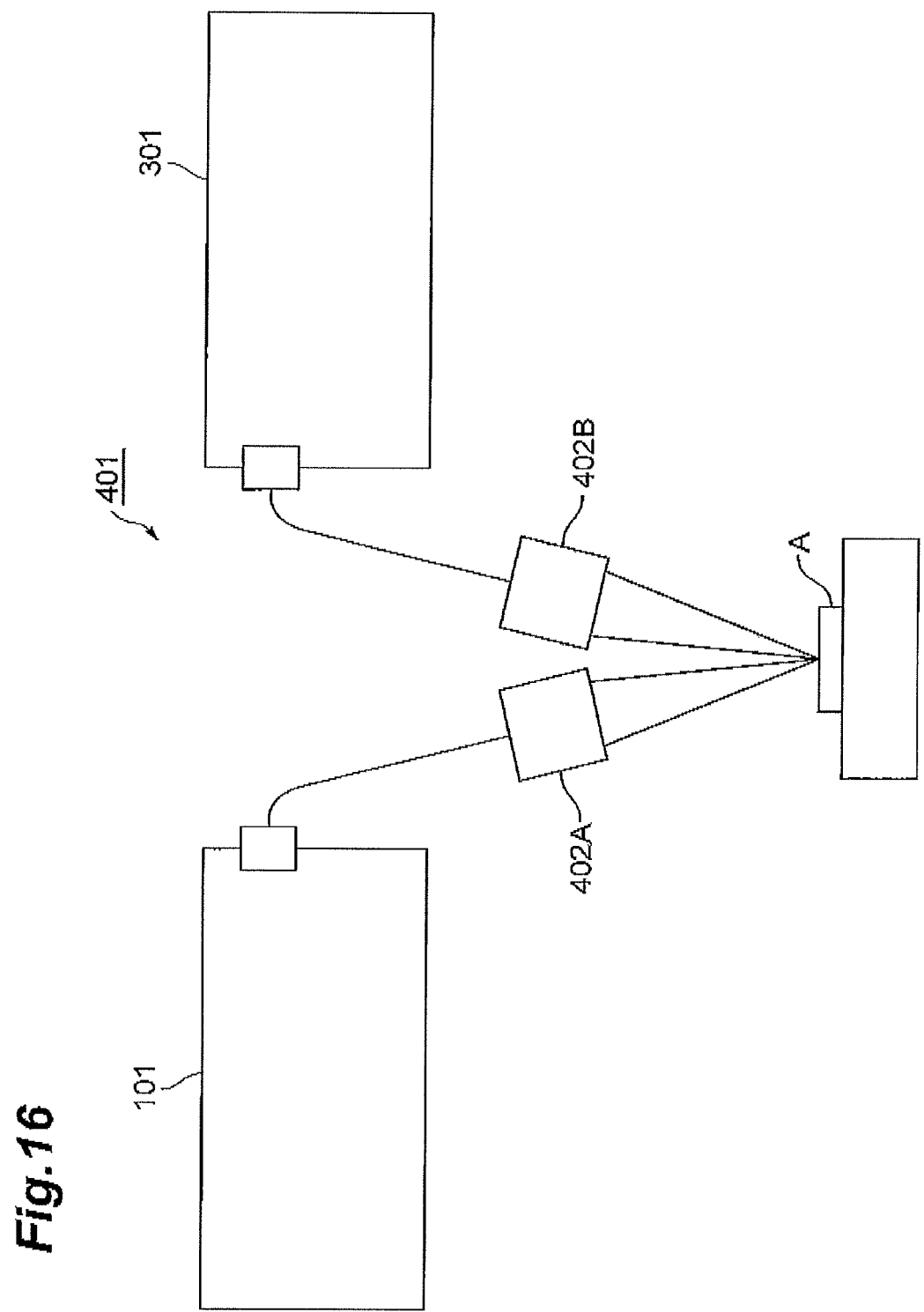
FIG. 16 is a schematic block diagram of a fluorescence detector system as an application example of the present invention.

Further, as an application example of the present invention, a fluorescence detector system 401, as shown in FIG. 16, in which the light source device 101 and the light detection device 301 are combined may be cited. In this fluorescence detector system 401, it is possible to irradiate a sample A with light output from the light source device 101 as an excitation light via a lens unit 402A, and fluorescence emitted from the sample A according to the irradiation is input to the light detection device 301 via a lens unit 402B, which makes it possible to detect the fluorescence in a predetermined wavelength range. Provided that the fluorescence detector system 401 is used, it is possible to freely adjust the wavelength range of an excitation light to be emitted and the wavelength range of fluorescence to be detected in a broad range. Here, in the case where the sample A limited to an extent is served as an object to be measured, the light source device 101 may be replaced with a general light source such as a laser light source.

As the dielectric thin film interference filters used in the respective embodiments described above of the present invention, in addition to the band pass filters, high-pass filters, low-pass filters, notch filters, and the like may be used.

Here, it is preferable that the n dielectric thin film interference filters be mounted so that the respective lines of intersections formed between the principal surface and the end planes have contact with the one inscribed circle. In this case, it is possible to equalize the ranges of incident angles of light to the respective dielectric thin film interference filters, which makes it possible to efficiently expand the variable range of selective wavelengths with respect to the limited area of the principal surface of the rotation supporting member.

Further, it is also preferable that the n dielectric thin film interference filters be respectively disposed to be located lateral to the inscribed circle on the principal surface. Provided that such a configuration is adopted, it is possible to further reduce the interference among the plurality of dielectric thin film interference filters.

Moreover, it is also preferable that the n dielectric thin film interference filters be disposed so that the lines connecting a predetermined point on the principal surface and the center points of the dielectric thin film interference filters form angles equal to one another therebetween. Provided that such dielectric thin film interference filters are used, it is possible to equalize the ranges of incident angles of light to the respective dielectric thin film interference filters, which makes it possible to efficiently expand the variable range of selective wavelengths with respect to the limited area of the rotation supporting member.

Furthermore, it is also preferable that the n dielectric thin film interference filters be disposed so as to be n-fold rotationally symmetric centering on a predetermined point on the principal surface. Provided that such a configuration is used, it is possible to further expand the variable range of selective wavelengths with respect to the limited area of the rotation supporting member.

Furthermore, it is also preferable that rotary shaft members for adjusting the inclination angles to the lines connecting a predetermined point on the principal surface and the center points of the dielectric thin film interference filters on the principal surface be respectively attached to the n dielectric thin film interference filters. Provided that such rotary shaft members are included, it is possible to adjust the range of incident angles of light to the dielectric thin film interference filters, which improves the convenience of the spectral device at the time of achieving a desired selective wavelength.

INDUSTRIAL APPLICABILITY

The present invention has a use application to use the spectral device that selects light in a predetermined wavelength range, thereby it is possible to easily expand the variable range of selective wavelengths without enlarging the device.

REFERENCE SIGNS LIST 11a to 11f: band pass filters, 15a to 15d: center points, 1, 101, 201: light source devices, 301: light detection device, 3: light source, 8, 8A, 8B, 8C, 8D, 108, 208, 308: filter rotating bodies, 10: rotary table (rotation supporting member), 10*a*: principal surface, 12: optical incidence plane (end plane), 13: optical emission plane (end plane), 17: inscribed circle, C$_1$: rotational center, L2, L4, L5: incident lights.

The invention claimed is:

1. A spectral device comprising:
   n (where n is an integer of 3 or more) dielectric thin film interference filters through which light from a light source is selectively transmitted within a wavelength range according to an incident angle of the light; and
   a tabular rotary supporting member in which the dielectric thin film interference filters are installed upright on a principal surface, and which is made rotatable around a predetermined point along the principal surface, wherein
   the n dielectric thin film interference filters are respectively disposed so that end planes on optical incidence sides or optical emission sides are inclined with respect to lines connecting the predetermined point on the principal surface of the rotary supporting member and center points of the dielectric thin film interference filters on the principal surface,
   the rotary supporting member is disposed such that the light is made incident at a position on a peripheral edge portion side of the principal surface with respect to the predetermined point thereon, and
   rotary shaft members attached in the vicinity of the center points of the dielectric thin film interference filters and configured to adjust the inclination angles of the optical incidence sides or the optical emission sides with respect to the lines connecting the predetermined point and the center points of the dielectric thin film interference filters,
   wherein the light has a width in a parallel direction with respect to the principal surface, and wherein the rotary supporting member is disposed such that the light includes the center point of the dielectric thin film interference filter in the width thereof, and
   wherein the dielectric thin film interference filters, which have the rotary shaft members at centers thereof, have a direction of rotation that is identical to that of the rotary supporting member.

2. The spectral device according to claim 1, wherein the n dielectric thin film interference filters are mounted so that respective lines of intersections formed between the principal surface and the end planes have contact with one inscribed circle.

3. The spectral device according to claim 2, wherein the n dielectric thin film interference filters are disposed so as to be respectively located lateral to the inscribed circle on the principal surface.

4. The spectral device according to claim 1, wherein the n dielectric thin film interference filters are disposed so that the lines connecting the predetermined point on the principal surface and the center points of the dielectric thin film interference filters on the principal surface form angles equal to one another therebetween.

5. The spectral device according to claim 4, wherein the n dielectric thin film interference filters are disposed so as to be n-fold rotationally symmetric centering on the predetermined point on the principal surface.

6. The spectral device according to claim 1, wherein the dielectric thin film interference filters are from three to six in number.

* * * * *